United States Patent
Bai et al.

(10) Patent No.: US 11,390,688 B2
(45) Date of Patent: Jul. 19, 2022

(54) ANTI-PCSK9 MONOCLONAL ANTIBODY

(71) Applicant: BEIJING DONGFANG BIOTECH CO., LTD., Beijing (CN)

(72) Inventors: Yi Bai, Beijing (CN); Xiaomin Li, Beijing (CN); Wen Zhang, Beijing (CN); Shengmei Wen, Beijing (CN)

(73) Assignee: BEIJING DONGFANG BIOTECH CO., LTD., Beijing (CN)

( * ) Notice: Subject to any disclaimer, the term of this patent is extended or adjusted under 35 U.S.C. 154(b) by 0 days.

(21) Appl. No.: 16/321,472

(22) PCT Filed: Dec. 29, 2017

(86) PCT No.: PCT/CN2017/119822
§ 371 (c)(1),
(2) Date: Jan. 29, 2019

(87) PCT Pub. No.: WO2018/133649
PCT Pub. Date: Jul. 26, 2018

(65) Prior Publication Data
US 2021/0277146 A1    Sep. 9, 2021

(30) Foreign Application Priority Data
Jan. 22, 2017   (CN) .......................... 201710052879.8

(51) Int. Cl.
*C07K 16/40*       (2006.01)
*A61K 35/17*       (2015.01)

(52) U.S. Cl.
CPC .............. *C07K 16/40* (2013.01); *A61K 35/17* (2013.01); *C07K 2317/14* (2013.01); *C07K 2317/565* (2013.01)

(58) Field of Classification Search
None
See application file for complete search history.

(56) References Cited

U.S. PATENT DOCUMENTS

2013/0344085 A1   12/2013   Wu et al.

FOREIGN PATENT DOCUMENTS

| CN | 102245641 A | 11/2011 |
|---|---|---|
| CN | 103261230 A | 8/2013 |
| CN | 105315371 A | 2/2016 |
| CN | 105348390 A | 2/2016 |
| CN | 106749670 A | 5/2017 |
| JP | 2014511106 A | 5/2014 |
| KR | 20130118925 A | 10/2013 |
| WO | 2014150983 A2 | 9/2014 |

OTHER PUBLICATIONS

Manal Alkindi et al. "Monoclonal Antibodies for the Treatment of Hypercholesterolemia: Targeting PCSK9". Canadian Journal of Cardiology. vol.32, No. 12, Dec. 1, 2016(Dec. 1, 2016). pp. 1552-1560.
EP extended Search Report dated Jun. 3, 2020 re: Application No. 17893120.0, pp. 1-14.
Xinlin Zhang et al. "Safety and efficacy of anti-PCSK9 antibodies: a meta-analysis of 25 randomized, controlled trials". BMC Medicine. vol. 55, No. 1, Jun. 23, 2015(Jun. 23, 2015). p. 2833, XP055215140, DOI: 10.1186/s12916-015-0358-8.
EP Partial Search Report dated Feb. 20, 2020 re: Application No. 17893120.0, pp. 1-15.
KR first Office Action dated Apr. 29, 2020 re: Application No. 10-2019-7003329, pp. 1-8.
Cao, Y. et al. Selection and characterization of human PCSK9 antibody from phage displayed antibody library. Biochemical and Biophysical Research Communications. Jun. 5, 2015 (Jun. 5, 2015), vol. 463, pp. 712-718.
JP first Office Action dated Jan. 6, 2020 re: Application No. 2019-505510, pp. 1-7.

*Primary Examiner* — Sharon X Wen
(74) *Attorney, Agent, or Firm* — Gang Yu

(57) ABSTRACT

The application discloses an anti-Proprotein Convertase Subtilisin/Kexin Type 9 (PCSK9) monoclonal antibody, an amino acid sequence comprising coded antibody variable regions and Complementarity-Determining Regions (CDR), the obtaining method, and application of monoclonal antibody. The anti-PCSK9 monoclonal antibodies are screened from a phage antibody library; affinity maturation is achieved by using a method that the phage antibody library is established by means of chain displacement; After screening the light chain CDR1, 2, 3 Mutant Library of monoclonal antibodies obtained from primary screening; monoclonal antibodies having high affinity are selected; then screening the mutant libraries of heavy chain CDR1, 2, 3 regions; and finally the monoclonal antibodies having high affinity are screened. The PCSK9 antibody obtained by the application has good affinity to PCSK9 and can inhibit the binding of PCSK9 with its ligand and can be used for treating dyslipidemia, cardiovascular and cerebrovascular diseases and thrombotic occlusion diseases.

13 Claims, 5 Drawing Sheets
Specification includes a Sequence Listing.

SEQUENCE LISTING

<160> NUMBER OF SEQ ID NOS: 67

<210> SEQ ID NO 1
<211> LENGTH: 115
<212> TYPE: PRT
<213> ORGANISM: Homo sapiens

<400> SEQUENCE: 1

Gln Val Gln Leu Val Gln Ser Gly Ala Glu Val Lys Arg Pro Gly Ala
1               5                   10                  15

Ser Val Lys Val Ser Cys Lys Ala Ser Gly Gly Thr Phe Thr Asn Asn
            20                  25                  30

Ala Ile Ser Trp Val Arg Gln Ala Pro Gly Gln Gly Leu Glu Trp Met
        35                  40                  45

Gly Arg Ile Ile Pro Met Phe Gly Met Ala Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Gly Ile Pro Met Ile Trp Gly Gln Gly Thr Thr Val Thr
            100                 105                 110

Val Ser Ser
        115

<210> SEQ ID NO 2
<211> LENGTH: 115
<212> TYPE: PRT
<213> ORGANISM: Homo sapiens

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Val Thr Ser Tyr
            20                  25                  30

Gly Ile Ser Trp Val Arg Gln Ala Pro Gly Gln Gly Leu Glu Trp Met
        35                  40                  45

Gly Trp Leu Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Ser Leu Asp Val Trp Gly Gln Gly Thr Thr Val Thr
            100                 105                 110

Val Ser Ser
        115

<210> SEQ ID NO 3
<211> LENGTH: 115
<212> TYPE: PRT
<213> ORGANISM: Homo sapiens

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Val Thr Ser Tyr
            20                  25                  30

-continued

Gly Ile Ser Trp Val Arg Gln Ala Pro Gly Gln Gly Leu Glu Trp Met
            35                  40                  45

Gly Trp Val Ser Phe Tyr Asn Gly Gln Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Ser Leu Asp Val Trp Gly Gln Gly Thr Thr Val Thr
                100                 105                 110

Val Ser Ser
        115

<210> SEQ ID NO 4
<211> LENGTH: 115
<212> TYPE: PRT
<213> ORGANISM: Homo sapiens

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Val Thr Ser Tyr
            20                  25                  30

Gly Ile Ser Trp Val Arg Gln Ala Pro Gly Gln Gly Leu Glu Trp Met
            35                  40                  45

Gly Trp Val Ser Phe Tyr Asn Gly Asn Ser Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Ser Leu Asp Val Trp Gly Gln Gly Thr Thr Val Thr
                100                 105                 110

Val Ser Ser
        115

<210> SEQ ID NO 5
<211> LENGTH: 115
<212> TYPE: PRT
<213> ORGANISM: Homo sapiens

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Thr Ser Tyr
            20                  25                  30

Gly Ile Ser Trp Val Arg Gln Ala Pro Gly Gln Gly Leu Glu Trp Met
            35                  40                  45

Gly Trp Val Ser Phe Tyr Asn Gly Asn Ser Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Phe Gly Met Asp Arg Trp Gly Gln Gly Thr Thr Val Thr
                100                 105                 110

Val Ser Ser
        115

<210> SEQ ID NO 6
<211> LENGTH: 115
<212> TYPE: PRT
<213> ORGANISM: Homo sapiens

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Val Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Gln Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Phe Gly Met Asp Arg Trp Gly Gln Gly Thr Thr Val Thr
            100                 105                 110

Val Ser Ser
        115

<210> SEQ ID NO 7
<211> LENGTH: 115
<212> TYPE: PRT
<213> ORGANISM: Homo sapiens

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Gln Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Ser Ile Trp Gly Gln Gly Thr Thr Val Thr
            100                 105                 110

Val Ser Ser
        115

<210> SEQ ID NO 8
<211> LENGTH: 115
<212> TYPE: PRT
<213> ORGANISM: Homo sapiens

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Gln Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Thr Val Trp Gly Gln Gly Thr Thr Val Thr
            100                 105                 110

Val Ser Ser
        115

<210> SEQ ID NO 9
<211> LENGTH: 115
<212> TYPE: PRT
<213> ORGANISM: Homo sapiens

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Thr Ser Tyr
            20                  25                  30

Gly Ile Ser Trp Val Arg Gln Ala Pro Gly Gln Gly Leu Glu Trp Met
        35                  40                  45

Gly Trp Val Thr Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Phe Gly Leu Ser Val Trp Gly Gln Gly Thr Thr Val Thr
            100                 105                 110

Val Ser Ser
        115

<210> SEQ ID NO 10
<211> LENGTH: 115
<212> TYPE: PRT
<213> ORGANISM: Homo sapiens

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Gln Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

-continued

Ala Arg Gly Phe Gly Met Asp Arg Trp Gly Gln Gly Thr Thr Val Thr
            100                 105                 110

Val Ser Ser
        115

<210> SEQ ID NO 11
<211> LENGTH: 107
<212> TYPE: PRT
<213> ORGANISM: Homo sapiens

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asn Arg
            20                  25                  30

Leu Thr Trp Tyr Gln Gln Lys Pro Gly Lys Ala Pro Lys Leu Leu Ile
        35                  40                  45

Tyr Asp Ala Ser Ser Arg Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Glu Asn Asp Pro Thr
                85                  90                  95

Thr Phe Gly Gln Gly Thr Lys Val Glu Ile Lys
            100                 105

<210> SEQ ID NO 12
<211> LENGTH: 107
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Arg Asn Trp
            20                  25                  30

Leu Asp Trp Tyr Gln Gln Lys Pro Gly Lys Ala Pro Lys Leu Leu Ile
        35                  40                  45

Tyr Gly Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Asn Asp Ile Pro Leu
                85                  90                  95

Thr Phe Gly Gln Gly Thr Lys Val Glu Ile Lys
            100                 105

<210> SEQ ID NO 13
<211> LENGTH: 107
<212> TYPE: PRT
<213> ORGANISM: Homo sapiens

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Trp
            20                  25                  30

Leu Asn Trp Tyr Gln Gln Lys Pro Gly Lys Ala Pro Lys Leu Leu Ile

```
                35                  40                  45

Tyr Ala Ala Ser Thr Arg Glu Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Trp Asn Asn Thr Pro Asn
                 85                  90                  95

Thr Phe Gly Gln Gly Thr Lys Val Glu Ile Lys
            100                 105

<210> SEQ ID NO 14
<211> LENGTH: 107
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asn Val Asn Asn Trp
             20                  25                  30

Leu Asn Trp Tyr Gln Gln Lys Pro Gly Lys Ala Pro Lys Leu Leu Ile
         35                  40                  45

Tyr Ala Ala Ser Thr Arg Glu Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Asn Asp Met Pro Leu
                 85                  90                  95

Thr Phe Gly Gln Gly Thr Lys Val Glu Ile Lys
            100                 105

<210> SEQ ID NO 15
<211> LENGTH: 107
<212> TYPE: PRT
<213> ORGANISM: Homo sapiens

<400> SEQUENCE: 15

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asn Ile Asn Ser Trp
             20                  25                  30

Leu Asn Trp Tyr Gln Gln Lys Pro Gly Lys Ala Pro Lys Leu Leu Ile
         35                  40                  45

Tyr Gly Ala Ser Ser Arg Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Trp Phe Asp Val Pro Thr
                 85                  90                  95

Thr Phe Gly Gln Gly Thr Lys Val Glu Ile Lys
            100                 105

<210> SEQ ID NO 16
<211> LENGTH: 107
<212> TYPE: PRT
<213> ORGANISM: Homo sapiens

<400> SEQUENCE: 16
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Asn Trp
            20                  25                  30

Leu Asn Trp Tyr Gln Gln Lys Pro Gly Lys Ala Pro Lys Leu Leu Ile
        35                  40                  45

Tyr Gly Ala Ser Thr Arg Pro Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Asp Asp Thr Pro Asn
                85                  90                  95

Thr Phe Gly Gln Gly Thr Lys Val Glu Ile Lys
                100                 105
```

<210> SEQ ID NO 17
<211> LENGTH: 107
<212> TYPE: PRT
<213> ORGANISM: Homo sapiens

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile His Asn Trp
            20                  25                  30

Leu Asn Trp Tyr Gln Gln Lys Pro Gly Lys Ala Pro Lys Leu Leu Ile
        35                  40                  45

Tyr Asp Ala Ser Asn Arg Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Ser Asn Ile Pro Leu
                85                  90                  95

Thr Phe Gly Gln Gly Thr Lys Val Glu Ile Lys
                100                 105
```

<210> SEQ ID NO 18
<211> LENGTH: 107
<212> TYPE: PRT
<213> ORGANISM: Homo sapiens

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Ser Trp
            20                  25                  30

Leu Thr Trp Tyr Gln Gln Lys Pro Gly Lys Ala Pro Lys Leu Leu Ile
        35                  40                  45

Tyr Gly Ala Ser Asn Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ser Lys Ile Pro Leu
                85                  90                  95

Thr Phe Gly Gln Gly Thr Lys Val Glu Ile Lys
                100                 105
```

<210> SEQ ID NO 19
<211> LENGTH: 107
<212> TYPE: PRT
<213> ORGANISM: Homo sapiens

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Arg Asn Trp
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Thr Asp Thr Pro Leu
                85                  90                  95

Thr Phe Gly Gln Gly Thr Lys Val Glu Ile Lys
            100                 105

<210> SEQ ID NO 20
<211> LENGTH: 107
<212> TYPE: PRT
<213> ORGANISM: Homo sapiens

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Arg Asn Trp
            20                  25                  30

Leu Thr Trp Tyr Gln Gln Lys Pro Gly Lys Ala Pro Lys Leu Leu Ile
        35                  40                  45

Tyr Gly Ala Ser Asn Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Asp Ser Thr Pro Pro
                85                  90                  95

Thr Phe Gly Gln Gly Thr Lys Val Glu Ile Lys
            100                 105

<210> SEQ ID NO 21
<211> LENGTH: 107
<212> TYPE: PRT
<213> ORGANISM: Homo sapiens

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Tyr
            20                  25                  30

Leu Asn Trp Tyr Gln Gln Lys Pro Gly Lys Ala Pro Lys Leu Leu Ile
        35                  40                  45

Tyr Asp Ala Ser Ser Arg Pro Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ser Met Pro Met
                85                  90                  95

Thr Phe Gly Gln Gly Thr Lys Val Glu Ile Lys
            100                 105

<210> SEQ ID NO 22
<211> LENGTH: 11
<212> TYPE: PRT
<213> ORGANISM: Homo sapiens

<400> SEQUENCE: 22

Arg Ala Ser Gln Ser Ile Asp Asn Arg Leu Thr
1               5                   10

<210> SEQ ID NO 23
<211> LENGTH: 11
<212> TYPE: PRT
<213> ORGANISM: Homo sapiens

<400> SEQUENCE: 23

Arg Ala Ser Gln Ser Val Arg Asn Trp Leu Asp
1               5                   10

<210> SEQ ID NO 24
<211> LENGTH: 11
<212> TYPE: PRT
<213> ORGANISM: Homo sapiens

<400> SEQUENCE: 24

Arg Ala Ser Gln Gly Ile Asn Ser Trp Leu Asn
1               5                   10

<210> SEQ ID NO 25
<211> LENGTH: 11
<212> TYPE: PRT
<213> ORGANISM: Homo sapiens

<400> SEQUENCE: 25

Arg Ala Ser Gln Asn Val Asn Asn Trp Leu Asn
1               5                   10

<210> SEQ ID NO 26
<211> LENGTH: 11
<212> TYPE: PRT
<213> ORGANISM: Homo sapiens

<400> SEQUENCE: 26

Arg Ala Ser Gln Asn Ile Asn Ser Trp Leu Asn
1               5                   10

<210> SEQ ID NO 27
<211> LENGTH: 11
<212> TYPE: PRT
<213> ORGANISM: Homo sapiens

<400> SEQUENCE: 27

Arg Ala Ser Gln Asn Ile Asn Asn Trp Leu Asn
1               5                   10

<210> SEQ ID NO 28
<211> LENGTH: 11
<212> TYPE: PRT

<213> ORGANISM: Homo sapiens

<400> SEQUENCE: 28

Arg Ala Ser Gln Gly Ile His Asn Trp Leu Asn
1               5                   10

<210> SEQ ID NO 29
<211> LENGTH: 11
<212> TYPE: PRT
<213> ORGANISM: Homo sapiens

<400> SEQUENCE: 29

Arg Ala Ser Gln Asp Val Asp Ser Trp Leu Thr
1               5                   10

<210> SEQ ID NO 30
<211> LENGTH: 11
<212> TYPE: PRT
<213> ORGANISM: Homo sapiens

<400> SEQUENCE: 30

Arg Ala Ser Gln Ser Val Arg Asn Trp Leu Asn
1               5                   10

<210> SEQ ID NO 31
<211> LENGTH: 11
<212> TYPE: PRT
<213> ORGANISM: Homo sapiens

<400> SEQUENCE: 31

Arg Ala Ser Gln Asp Val Arg Asn Trp Leu Thr
1               5                   10

<210> SEQ ID NO 32
<211> LENGTH: 11
<212> TYPE: PRT
<213> ORGANISM: Homo sapiens

<400> SEQUENCE: 32

Arg Ala Ser Gln Ser Ile Arg Ser Tyr Leu Asn
1               5                   10

<210> SEQ ID NO 33
<211> LENGTH: 7
<212> TYPE: PRT
<213> ORGANISM: Homo sapiens

<400> SEQUENCE: 33

Asp Ala Ser Ser Arg Gln Ser
1               5

<210> SEQ ID NO 34
<211> LENGTH: 7
<212> TYPE: PRT
<213> ORGANISM: Homo sapiens

<400> SEQUENCE: 34

Gly Ala Ser Thr Leu Glu Ser
1               5

<210> SEQ ID NO 35
<211> LENGTH: 7
<212> TYPE: PRT
<213> ORGANISM: Homo sapiens

```
<400> SEQUENCE: 35

Ala Ala Ser Thr Arg Glu Thr
1               5

<210> SEQ ID NO 36
<211> LENGTH: 7
<212> TYPE: PRT
<213> ORGANISM: Homo sapiens

<400> SEQUENCE: 36

Gly Ala Ser Ser Arg Gln Ser
1               5

<210> SEQ ID NO 37
<211> LENGTH: 7
<212> TYPE: PRT
<213> ORGANISM: Homo sapiens

<400> SEQUENCE: 37

Gly Ala Ser Thr Arg Pro Thr
1               5

<210> SEQ ID NO 38
<211> LENGTH: 7
<212> TYPE: PRT
<213> ORGANISM: Homo sapiens

<400> SEQUENCE: 38

Asp Ala Ser Asn Arg Gln Ser
1               5

<210> SEQ ID NO 39
<211> LENGTH: 7
<212> TYPE: PRT
<213> ORGANISM: Homo sapiens

<400> SEQUENCE: 39

Gly Ala Ser Asn Leu Ala Ser
1               5

<210> SEQ ID NO 40
<211> LENGTH: 7
<212> TYPE: PRT
<213> ORGANISM: Homo sapiens

<400> SEQUENCE: 40

Asp Ala Ser Asn Leu Gln Ser
1               5

<210> SEQ ID NO 41
<211> LENGTH: 7
<212> TYPE: PRT
<213> ORGANISM: Homo sapiens

<400> SEQUENCE: 41

Asp Ala Ser Ser Arg Pro Thr
1               5

<210> SEQ ID NO 42
<211> LENGTH: 9
<212> TYPE: PRT
<213> ORGANISM: Homo sapiens

<400> SEQUENCE: 42
```

Gln Gln Pro Glu Asn Asp Pro Thr Thr
1               5

<210> SEQ ID NO 43
<211> LENGTH: 9
<212> TYPE: PRT
<213> ORGANISM: Homo sapiens

<400> SEQUENCE: 43

Gln Gln Asp Asn Asp Ile Pro Leu Thr
1               5

<210> SEQ ID NO 44
<211> LENGTH: 9
<212> TYPE: PRT
<213> ORGANISM: Homo sapiens

<400> SEQUENCE: 44

Gln Gln Trp Asn Asn Thr Pro Asn Thr
1               5

<210> SEQ ID NO 45
<211> LENGTH: 9
<212> TYPE: PRT
<213> ORGANISM: Homo sapiens

<400> SEQUENCE: 45

Gln Gln Asp Asn Asp Met Pro Leu Thr
1               5

<210> SEQ ID NO 46
<211> LENGTH: 9
<212> TYPE: PRT
<213> ORGANISM: Homo sapiens

<400> SEQUENCE: 46

Gln Gln Trp Phe Asp Val Pro Thr Thr
1               5

<210> SEQ ID NO 47
<211> LENGTH: 9
<212> TYPE: PRT
<213> ORGANISM: Homo sapiens

<400> SEQUENCE: 47

Gln Gln Trp Asp Asp Thr Pro Asn Thr
1               5

<210> SEQ ID NO 48
<211> LENGTH: 9
<212> TYPE: PRT
<213> ORGANISM: Homo sapiens

<400> SEQUENCE: 48

Gln Gln Asn Ser Asn Ile Pro Leu Thr
1               5

<210> SEQ ID NO 49
<211> LENGTH: 9
<212> TYPE: PRT
<213> ORGANISM: Homo sapiens

<400> SEQUENCE: 49

Gln Gln Asp Ser Lys Ile Pro Leu Thr
1               5

<210> SEQ ID NO 50
<211> LENGTH: 9
<212> TYPE: PRT
<213> ORGANISM: Homo sapiens

<400> SEQUENCE: 50

Gln Gln Trp Thr Asp Thr Pro Leu Thr
1               5

<210> SEQ ID NO 51
<211> LENGTH: 9
<212> TYPE: PRT
<213> ORGANISM: Homo sapiens

<400> SEQUENCE: 51

Gln Gln Asp Asp Ser Thr Pro Pro Thr
1               5

<210> SEQ ID NO 52
<211> LENGTH: 9
<212> TYPE: PRT
<213> ORGANISM: Homo sapiens

<400> SEQUENCE: 52

Gln Gln Gly Asp Ser Met Pro Met Thr
1               5

<210> SEQ ID NO 53
<211> LENGTH: 8
<212> TYPE: PRT
<213> ORGANISM: Homo sapiens

<400> SEQUENCE: 53

Gly Gly Thr Phe Thr Asn Asn Ala
1               5

<210> SEQ ID NO 54
<211> LENGTH: 8
<212> TYPE: PRT
<213> ORGANISM: Homo sapiens

<400> SEQUENCE: 54

Gly Tyr Thr Val Thr Ser Tyr Gly
1               5

<210> SEQ ID NO 55
<211> LENGTH: 8
<212> TYPE: PRT
<213> ORGANISM: Homo sapiens

<400> SEQUENCE: 55

Gly Tyr Ser Leu Thr Ser Tyr Gly
1               5

<210> SEQ ID NO 56
<211> LENGTH: 9
<212> TYPE: PRT
<213> ORGANISM: Homo sapiens

<400> SEQUENCE: 56

Arg Ile Ile Pro Met Phe Gly Met Ala
1               5

```
<210> SEQ ID NO 57
<211> LENGTH: 9
<212> TYPE: PRT
<213> ORGANISM: Homo sapiens

<400> SEQUENCE: 57

Trp Leu Ser Phe Tyr Asn Gly Asn Thr
1               5

<210> SEQ ID NO 58
<211> LENGTH: 9
<212> TYPE: PRT
<213> ORGANISM: Homo sapiens

<400> SEQUENCE: 58

Trp Val Thr Phe Tyr Asn Gly Asn Thr
1               5

<210> SEQ ID NO 59
<211> LENGTH: 9
<212> TYPE: PRT
<213> ORGANISM: Homo sapiens

<400> SEQUENCE: 59

Trp Val Ser Phe Tyr Gln Gly Asn Thr
1               5

<210> SEQ ID NO 60
<211> LENGTH: 9
<212> TYPE: PRT
<213> ORGANISM: Homo sapiens

<400> SEQUENCE: 60

Trp Val Ser Phe Tyr Asn Gly Gln Thr
1               5

<210> SEQ ID NO 61
<211> LENGTH: 9
<212> TYPE: PRT
<213> ORGANISM: Homo sapiens

<400> SEQUENCE: 61

Trp Val Ser Phe Tyr Asn Gly Asn Ser
1               5

<210> SEQ ID NO 62
<211> LENGTH: 8
<212> TYPE: PRT
<213> ORGANISM: Homo sapiens

<400> SEQUENCE: 62

Ala Arg Glu Gly Ile Pro Met Ile
1               5

<210> SEQ ID NO 63
<211> LENGTH: 8
<212> TYPE: PRT
<213> ORGANISM: Homo sapiens

<400> SEQUENCE: 63

Ala Arg Gly Tyr Ser Leu Asp Val
1               5

<210> SEQ ID NO 64
<211> LENGTH: 8
```

```
<212> TYPE: PRT
<213> ORGANISM: Homo sapiens

<400> SEQUENCE: 64

Ala Arg Gly Tyr Gly Met Ser Ile
1               5

<210> SEQ ID NO 65
<211> LENGTH: 8
<212> TYPE: PRT
<213> ORGANISM: Homo sapiens

<400> SEQUENCE: 65

Ala Arg Gly Phe Gly Met Asp Arg
1               5

<210> SEQ ID NO 66
<211> LENGTH: 8
<212> TYPE: PRT
<213> ORGANISM: Homo sapiens

<400> SEQUENCE: 66

Ala Arg Gly Tyr Gly Met Thr Val
1               5

<210> SEQ ID NO 67
<211> LENGTH: 8
<212> TYPE: PRT
<213> ORGANISM: Homo sapiens

<400> SEQUENCE: 67

Ala Arg Gly Phe Gly Leu Ser Val
1               5
```

ANTI-PCSK9 MONOCLONAL ANTIBODY

SEQUENCE LISTING

The present application contains a Sequence Listing which has been submitted electronically in ASCII format on Jan. 29, 2019 and is hereby incorporated by reference in its entirety. Said ASCII copy is named_PN100140DFBT_Sequence_list.txt and is 27.7 kilobytes in size, and contains 67 sequences which are identical to the sequence listing filed in the corresponding international application No: PCT/CN2017/119822 filed on Dec. 29, 2017.

TECHNICAL FIELD

The disclosure relates to the technical field of antibody engineering, and in particular to a fully human anti-Proprotein Convertase Subtilisin/Kexin Type 9 (PCSK9) monoclonal antibody, obtaining method and application thereof.

BACKGROUND

Proprotein Convertase Subtilisin/Kexin Type 9 (PCSK9) belongs to a proteinase K subfamily of proprotein convertase. The human PCSK9 gene is located at chromosome 1p32.3, has a length about 22 kb, has 12 exons and is capable of encoding a protein having 692 amino acid residues. The PCSK9 protein is composed of a signal peptide, a front structural domain, a catalytic domain and a carboxyl terminal structural domain (V structural domain), is synthesized as a soluble precursor of 74 kDa, and is capable of generating propeptide of 14 kDa and mature protease of 60 kDa by means of catalytic cracking of self in an endoplasmic reticulum. The PCSK9 is mainly expressed in livers, intestinal tracts and kidneys, and is also slightly expressed in skin and nerve systems, but only the PCSK9 in the livers can be secreted into blood circulation systems.

Research shows that the PCSK9 is capable of mediating degradation of a Low Density Lipoprotein Receptor (LDLR) to regulate the level of Low-Density Lipoprotein-Cholesterol (LDL-C) in plasma, and the LDL endocytosis process mediated with LDLR in liver is a main way for eliminating LDL from circulatory system. The LDLR is a protein having multiple structural domains, and its extracellular domain is tightly connected with epidermal growth factor precursor homologous structural domains EGF-A, EGF-B and EGF-C. When degradation of the LDLR is mediated with the PCSK9, the PCSK9 firstly needs to be bound with the LDLR, the LDLR mainly has a binding site which is mainly EGF-A, and a composition of the PCSK9 and the EGF-A is formed. Research shows that the PCSK9 is also capable of regulating cholesterol metabolism by means of a very low density lipoprotein receptor, an apolipoprotein B receptor and an apolipoprotein E receptor, but molecular mechanisms therein are not clear.

Basic study and clinical test show that inhibiting activity of the PCSK9 by means of echogenic interference measures, elimination of Low Density Lipoprotein (LDL) in the plasma can be accelerated, and thus a blood fat reduction function can be achieved. At present, PCSK9 inhibitors mainly include monoclonal antibodies, antisense nucleotides, small interfering Ribonucleic Acid (RNA), mimic peptides, small-molecule inhibitors, and the like.

The monoclonal antibody medicine is a research and development hotspot of a biomedicine field in the year, which has characteristics of being good in targeting property, high in specificity, low in toxic or side effect, and the like, This represents a latest development direction of a medicine treatment field. A monoclonal antibody having the PCSK9 as a target can be specifically combined with the PCSK9 and is capable of interdicting interactions of the PCSK9 and the LDLR and retarding a degradation process of the LDLR so as to take an effect of reducing the level of LDL-C. The clinical experimental data showed the safety, effectiveness and unique clinical disclosure values of anti-PCSK9 monoclonal antibody medicine.

A fully human antibody is a main direction of the development of therapeutic antibodies. Due to an antibody library technique, a good technical platform is provided for preparation and screening of human antibodies. Due to the antibody library technique, an essential hybridoma process in a conventional monoclonal antibody research process is avoided, and even various antibody genes and antibody molecular fragments can be obtained without an immunologic process. The phage antibody library is the earliest and most widely used antibody library at present. According to the source of antibody genes, the phage antibody library is divided into an immune library and a nonimmune library, and the nonimmune library also includes a natural library, a semisynthesis library and a complete synthesis library. An antibody affinity maturation process is simulated in screening of the phage antibody library, generally an antigen is coated by a solid phase medium, a phage antibody library to be screened is added, and multiple rounds of processes "adsorption, washing, elution and amplification" (that is, elutriation) are carried out till an antibody having high affinity specificity is screened.

At present, multiple pharmaceutical companies are actively developing monoclonal antibody medicine targeting at PCSK9. Repatha (evolocumab) of Amgen and Praluent (alirocumab) of Sanofi/Regeneron are both fully human antibodies, are approved to sell in 2015 successively and are applied to treat on primary hypercholesterolemia and familial hypercholesterolemia (heterozygote and homozygote). On the basis of statin, the LDL-C of a patient suffering from primary hypercholesterolemia can be reduced by 77% together with Evolocumab, the LDL-C of a patient suffering from heterozygote familial hypercholesterolemia can be reduced by 68%, and the LDL-C of a patient suffering from homozygote familial hypercholesterolemia can be reduced by 31%. The evolocumab has good tolerance and has no conspicuous security problem at present. A human monoclonal antibody bococizumab of Pfizer is at phase-III clinical test, and a human monoclonal antibody lodelcizumab of Novartis is at phase-Il clinical test. Roche and Merck are also having clinical test.

At present, China is still in lack of self-developed anti-PCSK9 fully human antibodies having high affinity in the field.

SUMMARY

The disclosure provides an anti-Proprotein Convertase Subtilisin/Kexin Type 9 (PCSK9) monoclonal antibody. Anti-PCSK9 monoclonal antibodies are screened from a complete synthesis antibody library; a small-capacity synthetic phage antibody light chain library is established by means of computer aided design and analysis; a library of mutations of light chain Complementarity-Determining Regions CDR1, 2, 3 of the anti-PCSK9 monoclonal antibodies is obtained by means of screening; after screening, monoclonal antibodies having high affinity are selected; a library is established to screen mutations at heavy chain regions CDR1, 2, 3 of the monoclonal antibodies; and finally an anti-PCSK9 monoclonal antibody having high affinity is obtained by means of screening. The anti-PCSK9 monoclonal antibody has completely new sequences, has good functions in vitro, particularly at a cellular level, and has very good medicinal disclosure prospects.

In order to achieve above purposes, the disclosure provides the anti-PCSK9 monoclonal antibody, including:

light chains and heavy chains; Light Complementarity-Determining Regions CDR1, CDR2 and CDR3 of the light chains are represented by LCDR1, LCDR2 and LCDR3 respectively; in addition, Heavy Complementarity-Determining Regions CDR1, CDR2 and CDR3 of the heavy chains are represented by HCDR1, HCDR2 and HCDR3 respectively; LCDR1 includes any one of RASQSIDNRLT (SEQ ID NO. 22), RASQSVRNWLD(SEQ ID NO. 23), RASQGINSWLN(SEQ ID NO. 24), RASQNVNNWLN (SEQ ID NO. 25), RASQNINSWLN(SEQ ID NO. 26), RASQNINNWLN(SEQ ID NO. 27), RASQGIHNWLN (SEQ ID NO. 28), RASQDVDSWLT(SEQ ID NO. 29), RASQSVRNWLN(SEQ ID NO. 30), RASQDVRNWLT (SEQ ID NO. 31) or RASQSIRSYLN(SEQ ID NO. 32); LCDR2 includes any one of DASSRQS(SEQ ID NO. 33), GASTLES(SEQ ID NO. 34), AASTRET(SEQ ID NO. 35), GASSRQS(SEQ ID NO. 36), GASTRPT(SEQ ID NO. 37), DASNRQS(SEQ ID NO. 38), GASNLAS(SEQ ID NO. 39), DASNLQS(SEQ ID NO. 40) or DASSRPT(SEQ ID NO. 41); LCDR3 includes any one of QQPENDPTT(SEQ ID NO. 42), QQDNDIPLT(SEQ ID NO. 43), QQWNNTPNT (SEQ ID NO. 44), QQDNDMPLT(SEQ ID NO. 45), QQWFDVPTT(SEQ ID NO. 46), QQWDDTPNT(SEQ ID NO. 47), QQNSNIPLT(SEQ ID NO. 48), QQDSKIPLT (SEQ ID NO. 49), QQWTDTPLT(SEQ ID NO. 50), QQDDSTPPT(SEQ ID NO. 51) or QQGDSMPMT(SEQ ID NO. 52); HCDR1 includes any one of GGTFTNNA(SEQ ID NO. 53), GYTVTSYG(SEQ ID NO. 54) or GYSLTSYG(SEQ ID NO. 55); HCDR2 includes any one of RIIPMFGMA(SEQ ID NO. 56), WLSFYNGNT(SEQ ID NO. 57), WVTFYNGNT(SEQ ID NO. 58), WVSFYQGNT(SEQ ID NO. 59), WVSFYNGQT(SEQ ID NO. 60) or WVSFYNGNS(SEQ ID NO. 61); HCDR3 includes AREGIPMI(SEQ ID NO. 62), ARGYSLDV(SEQ ID NO. 63), ARGYGMSI(SEQ ID NO. 64), ARGFGMDR(SEQ ID NO. 65), ARGYGMTV(SEQ ID NO. 66) or ARGFGLSV(SEQ ID NO. 67).

Herein, a light chain variable region amino acid sequence is preferably selected from any one SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20 or SEQ ID NO. 21.

Herein, a heavy chain variable region amino acid sequence is preferably selected from any one SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9 or SEQ ID NO. 10.

Herein, a heavy chain variable region HCDR1 sequence is selected from any one of GYTVTSYG(SEQ ID NO. 54) or GYSLTSYG(SEQ ID NO. 55); a light chain variable region LCDR1 sequence is selected from any one amino acid sequence of RASQSVRNWLD(SEQ ID NO. 23), RASQNVNNWLN(SEQ ID NO. 25), RASQNINSWLN (SEQ ID NO. 26), RASQNINNWLN(SEQ ID NO. 27) or RASQDVDSWLT(SEQ ID NO. 29); a heavy chain variable region HCDR2 sequence is selected from any one amino acid sequence of WVSFYQGNT(SEQ ID NO. 59), WVSFYNGQT(SEQ ID NO. 60) or WVSFYNGNS(SEQ ID NO. 61); a light chain variable region LCDR2 sequence is selected from any one amino acid sequence of GASTLES (SEQ ID NO. 34), AASTRET(SEQ ID NO. 35), GASSRQS (SEQ ID NO. 36), GASTRPT(SEQ ID NO. 37) or GASNLAS(SEQ ID NO. 39); a heavy chain variable region HCDR3 sequence is selected from any one amino acid sequence of ARGYSLDV(SEQ ID NO. 63), ARGYGMSI (SEQ ID NO. 64), ARGFGMDR(SEQ ID NO. 65) or ARGYGMTV(SEQ ID NO. 66); a light chain variable region LCDR3 sequence is selected from any one amino acid sequence of QQDNDIPLT(SEQ ID NO. 43), QQDNDMPLT(SEQ ID NO. 45), QQWFDVPTT(SEQ ID NO. 46), QQWDDTPNT(SEQ ID NO. 47) or QQDSKIPLT (SEQ ID NO. 49).

Herein, the disclosure further provides multiple antibodies, polypeptides or proteins having the above light chain or the heavy chain.

Herein, the disclosure further provides multiple antibodies having the above light chain or the heavy chain, the antibodies are capable of specifically binding with the PCSK9, interdicting binding of the PCSK9 with the LDLR, increasing the number of the LDLR on a cell surface or a level of the LDLR in a blood circulation system, and reducing the level of the LDL or the LDL-C in the blood circulation system.

Herein, the disclosure further provides a polynucleotide sequence or a combination having the above light chain or the heavy chain.

Herein, a heavy chain constant region of the anti-PCSK9 monoclonal antibody includes IgG1, IgG2, IgG3 and IgG4; and the light chain constant region includes $C_k$ or $C_\lambda$.

Herein, the heavy chain constant region preferably includes IgG4 or IgG2, and preferably an eukaryotic expression vector or a procaryotic organism expression vector of the heavy chain.

Herein, the light chain constant region preferably includes $C_k$, and preferably an eukaryotic expression vector or a procaryotic organism expression vector of the light chain.

Herein, the disclosure further provides a recombinant DNA expression vector having the polynucleotide sequence or the combination; a DNA sequence of the recombinant DNA expression vector includes a DNA sequence for encoding the anti-PCSK9 antibody in the above heavy chain variable region, the heavy chain constant region, the light chain variable region and the light chain constant region.

Herein, the disclosure further provides host cells transfected with the recombinant DNA expression vector, and the host cells include prokaryotic cell, yeast and insect cell or mammalian cell.

Herein, the prokaryotic cell is preferably *Escherichia coli*.

Herein, the mammalian cell is preferably Human Embryonic Kidney 293 (HEK293) cell, Chinese Hamster Ovary (CHO) cell or Myeloma (NS0) cell.

Herein, the disclosure further provides multiple whole-length antibodies, single-chain antibodies, single domain antibodies, bispecific antibodies and antibody-drug conjugates.

Herein, the disclosure further provides multiple monoclonal antibodies, artificial vectors, drugs or drug compositions having the above light chain or the heavy chain.

Herein, the monoclonal antibodies include whole-length antibodies and fragments of the anti-PCSK9 monoclonal antibody, and the fragments include, but not limited, Fab, Fab', F(ab')$_2$, Fv or ScFv.

Herein, the disclosure further provides a detection reagent or a kit having the above light chain or the heavy chain.

The antibody of the disclosure may be applied to diseases which are alleviated, relieved, inhibited or prevented by eliminating, inhibiting or reducing activity of the PCSK9, and the diseases include dyslipidemia, cardiovascular and cerebrovascular diseases and thrombotic occlusive diseases.

Herein, the dyslipidemia includes cholesterol increase, triglyceride increase, low-density lipoprotein increase and high-density lipoprotein reduction. The cardiovascular and cerebrovascular diseases include coronary arteriosclerotic heart diseases, acute myocardial infarction, atherosclerosis, stroke and peripheral artery occlusive diseases.

A method for obtaining the anti-PCSK9 monoclonal antibody, including:

(1) carrying out biopanning for an anti-PCSK9 single-chain antibody, and carrying out three rounds of enrichment screening of an antibody library to obtain an antibody sequence DFSK9-1 having high affinity from a completely synthetic ScFv phage library, a heavy chain DFSK9-H1 includes an amino acid sequence of SEQ ID NO. 1, and a light chain DFSK9-L1 includes an amino acid sequence of SEQ ID NO. 11;

(2) based on DFSK9-1, by means of Tertiary structure simulation of a computer, designing and establishing an antibody library of mutations light chain Complementarity-Determining Regions CDR1, CDR2 and CDR3, carrying out biopanning and positive cloning screening and identification on the antibody library of the mutations to obtain 10 single-chain antibody sequences having different light chains which are respectively named as DFSK9-2, DFSK9-3, DFSK9-4, DFSK9-5, DFSK9-6, DFSK9-7, DFSK9-8, DFSK9-9, DFSK9-10 and DFSK9-11, corresponding light chain variable regions are respectively named as DFSK9-L2, DFSK9-L3, DFSK9-L4, DFSK9-L5, DFSK9-L6, DFSK9-L7, DFSK9-L8, DFSK9-L9, DFSK9-L10 and DFSK9-L11, and corresponding amino acid sequences of the regions are respectively shown in SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20 and SEQ ID NO. 21; comparing affinity of the single-chain antibodies at a phage level;

(3) selecting five cloning DFSK9-2, DFSK9-4, DFSK9-5, DFSK9-6 and DFSK9-8, designing and establishing a mutation antibody library of heavy chain Complementarity-Determining Regions CDR1, CDR2 and CDR3, carrying out biopanning and positive cloning screening and identification on the heavy chain of the mutations of the heavy chain to obtain 10 different single-chain antibody sequences which are respectively named as DFSK9-12, DFSK9-13, DFSK9-14, DFSK9-15, DFSK9-16, DFSK9-17, DFSK9-18, DFSK9-19, DFSK9-20 and DFSK9-21; herein, DFSK9-12, DFSK9-13, DFSK9-14, DFSK9-15, DFSK9-16, DFSK9-17, DFSK9-18, DFSK9-19, DFSK9-20 and DFSK9-21 respectively have light chain variable region sequences of DFSK9-L2, DFSK9-L8, DFSK9-L5, DFSK9-L6, DFSK9-L5, DFSK9-L6, DFSK9-L5, DFSK9-L4, DFSK9-L6 and DFSK9-L6; corresponding amino acid sequences of the sequences are respectively shown in SEQ ID NO. 12, SEQ ID NO. 18, SEQ ID NO. 15, SEQ ID NO. 16, SEQ ID NO. 15, SEQ ID NO. 16, SEQ ID NO. 15, SEQ ID NO. 14, SEQ ID NO. 16 and SEQ ID NO. 16; DFSK9-12, DFSK9-13, DFSK9-14, DFSK9-15, DFSK9-16, DFSK9-17, DFSK9-18, DFSK9-19, DFSK9-20 and DFSK9-21 respectively have heavy chain variable region sequences of DFSK9-H2, DFSK9-H8, DFSK9-H7, DFSK9-H3, DFSK9-H6, DFSK9-H4, DFSK9-H4, DFSK9-H9, DFSK9-H5 and DFSK9-H10; corresponding amino acid sequences of these sequences are respectively shown in SEQ ID NO. 2, SEQ ID NO. 8, SEQ ID NO. 7, SEQ ID NO. 3, SEQ ID NO. 6, SEQ ID NO. 4, SEQ ID NO. 4, SEQ ID NO. 9, SEQ ID NO. 5 and SEQ ID NO. 10; comparing affinity of the single-chain antibodies at a phage level;

(4) cloning a heavy chain variable region gene and a light chain variable gene of the clones in (3) into an eukaryotic expression vector, transfecting a host cell, and obtaining a complete antibody of an anti-PCSK9 monoclonal antibody.

Herein, the CDR is a complementarity-determining region; the ScFv is single-chain fragment variable; the ADCs are antibody-drug conjugates; the LDLR is a Low Density Lipoprotein Receptor; the LDL-C is low Density Lipoprotein-Cholesterol; the HEK293E cell is a human embryonic kidney 293E cell; the CHO cell is a Chinese hamster ovary cell; the NS0 cell is a mouse NS0 thymoma cell.

Compared with conventional art, the disclosure has the beneficial effects that:

The disclosure provides multiple completely novel anti-PCSK9 antibodies which have high binding affinity with substrates, are capable of well interdicting binding of the PCSK9 with the LDLR, and in addition influences distribution and expression of the LDLR on the cell surface. Therefore, binding performance of the LDL-R with the LDL on the cell surface is improved, intake and degradation of the LDL by a cell are improved, and the purpose of reducing extracellular contents of the LDL and the LDL-C and reducing total cholesterol of the LDL and the LDL-C is achieved.

The monoclonal antibody provided by the disclosure may be used for eliminating, inhibiting or reducing activity of the PCSK9 to alleviate, relieve, inhibit or prevent diseases; the diseases include dyslipidemia, cardiovascular and cerebrovascular diseases and thrombotic occlusive diseases; the dyslipidemia includes cholesterol, triglyceride increase, low-density lipoprotein increase, high-density lipoprotein reduction, and the like; the cardiovascular and cerebrovascular diseases include coronary arteriosclerotic heart diseases, acute myocardial infarction, atherosclerosis, stroke, peripheral artery occlusive diseases, and the like.

DETAILED DESCRIPTION OF THE EMBODIMENTS

Figure 1:
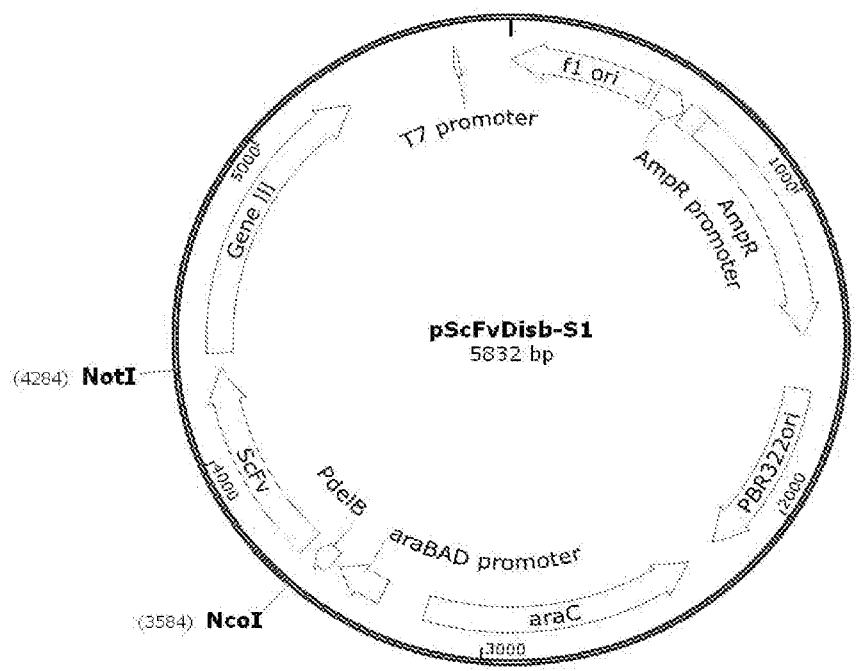
FIG. 1 shows a pScFvDisb-S1 plasmid profile.

Detailed implementation methods of the disclosure are shown in embodiments. The experimental methods and reagents described in the embodiments are conventional experimental methods and reagents without special description. The following are used only to illustrate and interpret the present disclosure, rather than limiting it in any way.

The disclosure provides one type of monoclonal antibody which is specifically binding with Proprotein Convertase Subtilisin/Kexin Type 9 (PCSK9), the heavy chain variable region sequence includes any one of SEQ ID NO. 1, 2, 3, 4, 5, 6, 7, 8, 9 and 10, and the light chain variable region sequence includes any one of SEQ ID NO. 11, 12, 13, 14, 15, 16, 17, 18, 19, 20 and 21.

Preferably, the heavy chain variable region sequence of the monoclonal antibody which is specifically binding with the PCSK9 is selected from any one of SEQ ID NO. 2, 3, 4, 5, 6, 7, 8, 9 and 10, and the light chain variable region sequence is selected from any one of SEQ ID NO. 12, 14, 15, 16 and 18.

By means of screening of a light chain phage library, the amino acid sequence of light chain Complementarity-Determining Regions LCDR1, LCDR2 and LCDR3 from an antibody light chain or functional fragments of the antibody light chain is selected from any one combination as follows (as shown in table 1):

antibody or a functional fragment are respectively represented by HCDR1, HCDR2 and HCDR3: HCDR1 is any one of GGTFTNNA(SEQ ID NO. 53), GYTVTSYG(SEQ ID NO. 54) or GYSLTSYG(SEQ ID NO. 55); HCDR2 is any one of RIIPMFGMA(SEQ ID NO. 56), WLSFYNGNT(SEQ ID NO. 57), WVTFYNGNT(SEQ ID NO. 58), WVSFYQGNT(SEQ ID NO. 59), WVSFYNGQT(SEQ ID NO. 60) or WVSFYNGNS(SEQ ID NO. 61); HCDR3 is any one of AREGIPMI(SEQ ID NO. 62), ARGYSLDV(SEQ ID NO. 63), ARGYGMSI(SEQ ID NO. 64), ARGFGMDR(SEQ ID NO. 65), ARGYGMTV(SEQ ID NO. 66) or ARGFGLSV(SEQ ID NO. 67).

Preferably, by means of screening of the heavy chain phage library, the monoclonal antibody which is specifically binding with the PCSK9 includes heavy chain variable regions of HCDR1, HCDR2 and HCDR3 and light chain variable regions of LCDR1, LCDR2 and LCDR3; herein, a sequence of the heavy chain variable region HCDR1 is an amino acid sequence selected from GYTVTSYG(SEQ ID NO. 54) or GYSLTSYG(SEQ ID NO. 55); a sequence of the light chain variable region LCDR1 is any one amino acid sequence selected from RASQSVRNWLD(SEQ ID NO. 23), RASQNVNNWLN(SEQ ID NO. 25), RASQNINSWLN(SEQ ID NO. 26), RASQNINNWLN (SEQ ID NO. 27) or RASQDVDSWLT(SEQ ID NO. 29); a sequence of the heavy chain variable region HCDR2 is any one amino acid sequence selected from WVSFYQGNT (SEQ ID NO. 59), WVSFYNGQT(SEQ ID NO. 60) or WVSFYNGNS(SEQ ID NO. 61); a sequence of the light chain variable region LCDR2 is any one amino acid

TABLE 1

Amino acid sequences of different CDFRs of the light chain

| No. | LCDR1 | LCDR2 | LCDR3 |
|---|---|---|---|
| A | RASQSIDNRLT (SEQ ID NO. 22) | DASSRQS (SEQ ID NO. 33) | QQPENDPTT (SEQ ID NO. 42) |
| B | RASQSVRNWLD (SEQ ID NO. 23) | GASTLES (SEQ ID NO. 34) | QQDNDIPLT (SEQ ID NO. 43) |
| C | RASQGINSWLN (SEQ ID NO. 24) | AASTRET (SEQID NO. 35) | QQWNNTPNT (SEQ ID NO. 44) |
| D | RASQNVNNWLN (SEQ ID NO. 25) | AASTRET (SEQ ID NO. 35) | QQDNDMPLT (SEQ ID NO. 45) |
| E | RASQNINSWLN (SEQ ID NO. 26) | GASSRQS (SEQ ID NO. 36) | QQWFDVPTT (SEQ ID NO. 46) |
| F | RASQNINNWLN (SEQ ID NO. 27) | GASTRPT (SEQ ID NO. 37) | QQWDDTPNT (SEQ ID NO. 47) |
| G | RASQGIHNWLN (SEQ ID NO. 28) | DASNRQS (SEQ ID NO. 38) | QQNSNIPLT (SEQ ID NO. 48) |
| H | RASQDVDSWLT (SEQ ID NO. 29) | GASNLAS (SEQ ID NO. 39) | QQDSKIPLT (SEQ ID NO. 49) |
| I | RASQSVRNWLN (SEQ ID No. 30) | DASNLQS (SEQ ID NO. 40) | QQWFDTPLT (SEQ ID NO. 50) |
| J | RASQDVRNWLT (SEQ ID NO. 31) | GASNLAS (SEQ ID NO. 39) | QQDDSTPPT (SEQ ID NO. 51) |
| K | RASQSIRSYLN (SEQ ID NO. 32) | DASSRPT (SEQ ID NO. 41) | QQGDSMPMT (SEQ ID NO. 52) |

By means of screening of a heavy chain phage library, the CDR1, CDR2 and CDR3 of the heavy chain from an sequence selected from GASTLES(SEQ ID NO. 34), AAS-TRET(SEQ ID NO. 35), GASSRQS(SEQ ID NO. 36), GASTRPT(SEQ ID NO. 37) or GASNLAS(SEQ ID NO. 39); a sequence of the heavy chain variable region HCDR3 is any one amino acid sequence selected from ARGYSLDV (SEQ ID NO. 63), ARGYGMSI(SEQ ID NO. 64), ARGFGMDR(SEQ ID NO. 65) or ARGYGMTV(SEQ ID NO. 66); a sequence of the light chain variable region LCDR3 is any one amino acid sequence selected from QQDNDIPLT(SEQ ID NO. 43), QQDNDMPLT(SEQ ID NO. 45), QQWFDVPTT(SEQ ID NO. 46), QQWDDTPNT (SEQ ID NO. 47) or QQDSKIPLT(SEQ ID NO. 49).

A method for obtaining a specific antibody by means of completely synthesizing a ScFv single-chain phage antibody library, the fully human monoclonal antibody which is specifically binding with the PCSK9 is obtained by means of screening by using a phage antibody library technique, including:

(1) carrying out biopanning for an anti-PCSK9 single-chain antibody, and carrying out three rounds of enrichment screening of an antibody library to obtain an antibody sequence DFSK9-1 having high affinity;

(2) based on DFSK9-1, by means of computer aided design, establishing a light chain CDR123 mutation library, and carrying out biopanning and positive clone screening and identification on the antibody library to obtain 10 different light chain antibody sequences including clones DFSK9-2, DFSK9-3, DFSK9-4, DFSK9-5, DFSK9-6, DFSK9-7, DFSK9-8, DFSK9-9, DFSK9-10 and DFSK9-11; Affinity comparison of the above 10 single chain antibodies at phage level;

(3) selecting five clones having high affinity, and establishing a heavy chain CDR123 library, carrying out biopanning and positive clone screening and identification on the antibody library to obtain single-chain antibodies with different sequences including DFSK9-12, DFSK9-13, DFSK9-14, DFSK9-15, DFSK9-16, DFSK9-17, DFSK9-18, DFSK9-19, DFSK9-20 and DFSK9-21; Affinity comparison of the single-chain antibodies at phage level;

(4) cloning a heavy chain variable region gene and a light chain variable gene of the clones in step (3) into an eukaryotic expression vector, transfected into a host cell to obtain a complete anti-PCSK9 monoclonal antibody.

Preferably, affinity and bioactivity test on the complete anti-PCSK9 monoclonal antibody of step (4) is further carried out.

SPECIFIC EMBODIMENTS

The present disclosure is described in detail below in connection with the drawings and embodiments.

Embodiment 1, Biopanning of an Anti-Proprotein Convertase Subtilisin/Kexin Type 9 (PCSK9) Monoclonal Antibody Modifying a pCom3 vector by means of gene cloning, naming the modified vector as pScFvDisb-S1 (as shown FIG. 1), and establishing a complete synthetic phage antibody library based on the vector.

Coating an antigen PCSK9-His 10 μg/1 ml/tube by an immune tube and overnight at 4° C. Blocking the immune tube and the phage antibody library (the amount of phage is about $10^9$-$10^{12}$) respectively by using PBST-4% milk for one hour at 37° C., putting the blocked phage antibody library into the immune tube to carry out antigen-antibody binding, and reacting for 1 hour at 37° C.; washing off unbound phage by using a Phosphate Buffered Solution-Phosphate Buffer Saline (PBST-PBS), eluting by using 0.1M of Glycine-HCl of pH2.2, and neutralizing by using 1.5M of a Tris-HCl of pH8.8 neutral eluant till about pH7.0; infecting 10 ml of the eluant to grow into an XL1-Blue bacterial liquid with an OD value is about 0.5-0.8, firstly leaving to stand for 30 minutes at 37° C., and carrying out shaking table oscillation culture for 1 hour at 150 rpm; carrying out gradient dilution on 1% of the bacterial liquid, coating a 2YTATG small plate, and calculating a yield of the phage; centrifuging the rest bacterial liquid, coating a 2YTATG large plate, and culturing overnight at 37° C.; transferring the bacterium cultured overnight into 2YTATG liquid culture medium, shaking till a logarithmic phase, adding M13K07 to assist phage infection, culturing at 28° C. overnight to amplify the phage, carrying out sedimentation purification on the phage with PEG6000-NaCl for a next round of screening, and carrying out three rounds of phage library enrichment and screening in all.

Embodiment 2, Screening of Positive Clones of Anti-Proprotein Convertase Subtilisin/Kexin Type 9 (PCSK9) Single Chain Antibody After three rounds of screening, selecting well partitioned monoclonal bacterial colonies, inoculating in a deep 96-well plate with 2YTATG liquid culture medium, culturing for 5 hours at 220 rpm and 37° C. till a logarithmic phase, putting about $10^{10}$ of helper phage M13K07 into each well, leaving to stand for 30 minutes at 37° C., and carrying out oscillation culture for 1 hour at 150 rpm; centrifuging for 15 minutes at 4000 rpm, resuspending precipitate in the 2YTATKA liquid culture medium, and culturing overnight at 220 rpm and 28° C.; centrifuging for 15 minutes at 4000 rpm at 4° C., and carrying out monoclonal Enzyme Linked Immunosorbent Assay (ELISA) identification on phage-containing supernate; screening an single-chain antibody DFSK9-1 having high affinity, the heavy chain variable region of the antibody is named as DFSK9-H1, and the amino acid sequence of the antibody is shown in SEQ ID NO. 1; the light chain variable region of the antibody is named as DFSK9-L1, and the amino acid sequence of the antibody is shown in SEQ ID NO. 11;

```
SEQ ID NO. 1 (DFSK9-H1 heavy chain variable region
sequence):
QVQLVQSGAEVKRPGASVKVSCKASGGTFTNNAISWVRQAPGQGLEWMGR
IIPMFGMANYAQKLQGRGTMTTDPSTSTAYMELRSLRSDDTAVYYCAREG
IPMIWGQGTTVTVSS SEQ ID NO. 11 (DFSK9-L1 light chain variable
region sequence):
DIQMTQSPSSLSASVGDRVTITCRASQSIDNRLTWYQQKPGKAPKLLIYD
ASSRQSGVPSRFSGSGSGTDFTLTISSLQPEDFATYYCQQPENDPTTFGQ
GTKVEIK
```

Embodiment 3, In-Vitro Affinity Maturation of Anti-Proprotein Convertase Subtilisin/Kexin Type 9 (PCSK9) Single Chain Antibody DFSK9-1

3.1 Establishment of a DFSK9-1 Light Chain CDR123 Mutation Library

Carrying out double-digestion on pScFvDisb-DFSK9-1 plasma by using NheI and NotI, carrying out agarose gel electrophoresis on a digestion product, cutting gel, and recycling strips of 5.5 kb; carrying out double-digestion on a synthetic light chain mutation library gene VLCDR123M by using NheI and NotI, and recycling a product by using a universal product recycling kit; connecting the mutation library gene with a vector for 4 hours by using T4 Deoxyribonucleic Acid (DNA) ligase at 16° C. according to a mole ratio of 3:1; transforming a connection product into XL1-Blue electrocompetent cells by using an electroporation method; at 37° C., carrying out vibration culture for one hour at 150 rpm to achieve anabiosis; diluting 1% bacterial liquid, coating a small plate, and calculating a library capacity; centrifuging other bacterial liquid for 15 minutes at 4000 rpm, coating precipitate to a 2YTATG large plate, inverting and culturing at 37° C. overnight; the library capacity of established antibody library is about $10^8$, randomly selecting 20 clones to carry out sequence analysis, and both the sequence accuracy rate and diversity are greater than 90%.

3.2 Biopanning of Phage Antibody Libraries and Screening of Positive Clones

Figure 2:
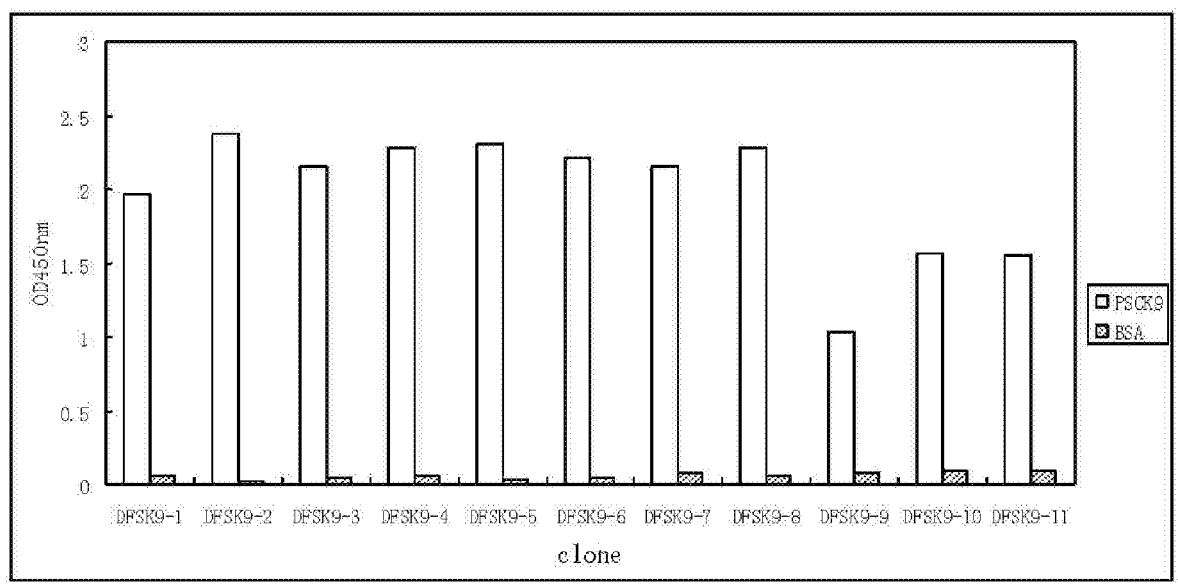
FIG. 2 shows relative affinity of the single-chain antibodies from positive cloning phage of a mutant light chain antibody library by Enzyme Linked Immunosorbent Assay (ELISA)

Carrying out biopanning and positive clone screening by using methods of the embodiment 1 and the embodiment 2, sequencing clones having high affinity to obtain 10 different single chain antibody sequences which are respectively named as DFSK9-2, DFSK9-3, DFSK9-4, DFSK9-5, DFSK9-6, DFSK9-7, DFSK9-8, DFSK9-9, DFSK9-10 and DFSK9-11, corresponding light chain variable region are named as DFSK9-L2, DFSK9-L3, DFSK9-L4, DFSK9-L5, DFSK9-L6, DFSK9-L7, DFSK9-L8, DFSK9-L9, DFSK9-L10 and DFSK9-L11, and corresponding amino acid sequences are respectively shown in SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20 and SEQ ID NO. 21; light chain variable region sequences SEQ ID NO. 12-SEQ ID NO. 21 as shown as follows:

Monoclonal phage ELISA identification results are shown in FIG. 2.

3.3 Identification of Relative Affinity of the Anti-PCSK9 Single-Chain Antibody by Means of Phage Horizontal Gradient Diluted Enzyme Linked Immunosorbent Assay (ELISA)

Carrying out monoclonal phage display and purification on the clones obtained in the embodiment 3.2, and carrying out phage horizontal gradient diluted ELISA identification on relative affinity of the monoclonal antibody.

Figure 3:
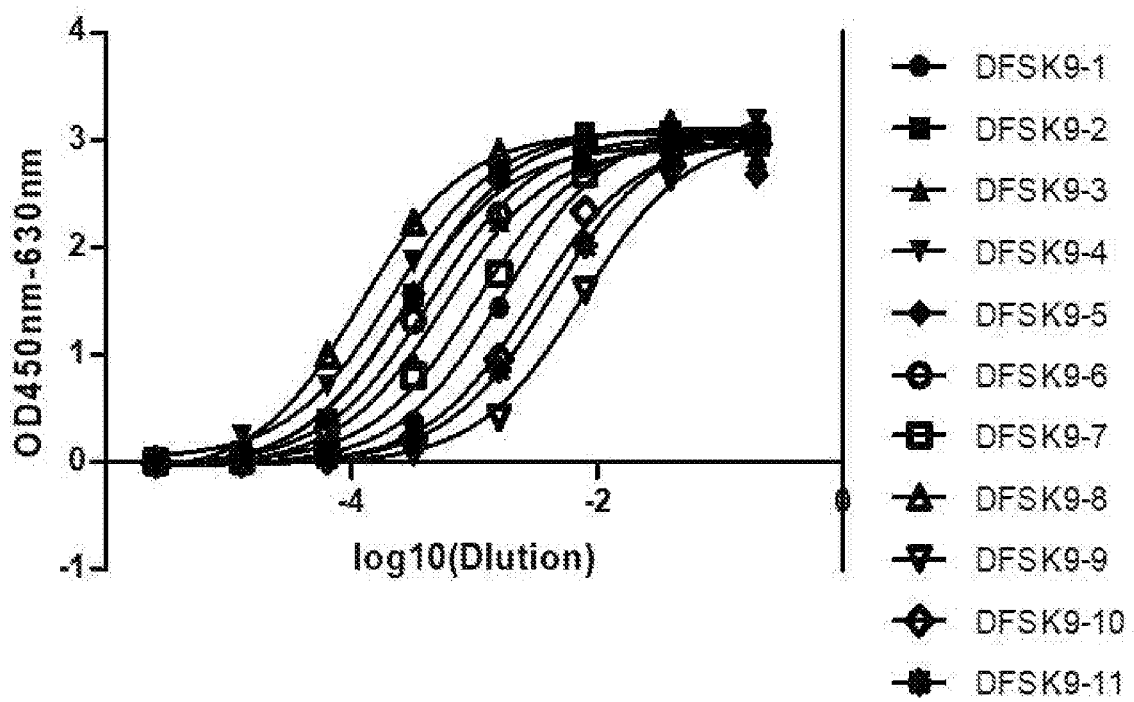
FIG. 3 shows relative affinity comparison of the single-chain antibody of the antibody library of the mutant light chain by means of positive cloning phage monoclonal gradient diluted ELISA.

Coating PCSK9-His (300 ng/well/100 μl) by 0.01M of Phosphate Buffer Saline (PBS) of pH7.2, and coating overnight at 4° C.; washing with Polybutylene Terephthalate (PBST) for three times, and sealing with PBST-4% milk at 37° C. for one hour; adding a purified phage sample (100 μl/well) which is diluted with PBST-4% milk for a 5-time gradient, and leaving to stand for one hour at 37° C.; washing with PBST for five times, adding an anti-M13-HRP monoclonal antibody (100 μl/well) which is diluted with PBST-4% milk in a ratio of 1:5000, and leaving to stand for one hour at 37° C.; developing by using a Tetramethylbenzidine (TMB) developing kit (100 μl/well) for 10 minutes at a room temperature, and terminating developing with 2M $H_2SO_4$ (50 μl/well); reading numbers by using a microplate reader at wavelengths of 450 nm and 630 nm; analyzing data and drawing pictures by using software GraphPad Prism 5Demo, and results are shown in FIG. 3. Results show that the screened phage single-chain antibodies all are capable of binding with PCSK9. The affinities of DFSK9-2, DFSK9-4, DFSK9-5, DFSK9-6 and DFSK9-8 with PCSK9 are remark-

```
SEQ ID NO. 12 (DFSK9-L2 light chain variable region sequence):
DIQMTQSPSSLSASVGDRVTITCRASQSVRNWLDWYQQKPGKAPKWYGAST
LESGVPSRFSGSGSGTDFTLTISSLQPEDFATYYCQQDNDIPLTFGQGTKVEIK SEQ ID NO. 13 (DFSK9-L3 light chain variable region sequence):
DIQMTQSPSSLSASVGDRVTITCRASQGINSWLNWYQQKPGKAPKLLIYAAST
RETGVPSRFSGSGSGTDFTLTISSLQPEDFATYYCQQWNNTPNTFGQGTKVEIK SEQ ID NO. 14 (DFSK9-L4 light chain variable region sequence):
DIQMTQSPSSLSASVGDRVTITCRASQNVNNWLNWYQQKPGKAPKLLIYAAST
RETGVPSRFSGSGSGTDFTLTISSLQPEDFATYYCQQDNDMPLTFGQGTKVEIK SEQ ID NO. 15 (DFSK9-L5 light chain variable region sequence):
DIQMTQSPSSLSASVGDRVTITCRASQNINSWLNWYQQKPGKAPKLLIYGASS
RQSGVPSRFSGSGSGTDFTLTISSLQPEDFATYYCQQWFDVPTTFGQGTKVEIK SEQ ID NO. 16 (DFSK9-L6 light chain variable region sequence):
DIQMTQSPSSLSASVGDRVTITCRASQNINNWLNWYQQKPGKAPKLLIYGAST
RPTGVPSRFSGSGSGTDFTLTISSLQPEDFATYYCQQWDDTPNTFGQGTKVEIK SEQ ID NO. 17 (DFSK9-L7 light chain variable region sequence):
DIQMTQSPSSLSASVGDRVTITCRASQGIHNWLNWYQQKPGKAPKLLIYDASN
RQSGVPSRFSGSGSGTDFTLTISSLQPEDFATYYCQQNSNIPLTFGQGTKVEIK SEQ ID NO. 18 (DFSK9-L8 light chain variable region sequence):
DIQMTQSPSSLSASVGDRVTITCRASQDVDSWLTWYQQKPGKAPKLLIYGASN
LASGVPSRFSGSGSGTDFTLTISSLQPEDFATYYCQQDSKIPLTFGQGTKVEIK SEQ ID NO. 19 (DFSK9-L9 light chain variable region sequence):
DIQMTQSPSSLSASVGDRVTITCRASQSVRNWLNWYQQKPGKAPKLLIYDASN
LQSGVPSRFSGSGSGTDFTLTISSLQPEDFATYYCQQWTDTPLTFGQGTKVEIK SEQ ID NO. 20 (DFSK9-L10 light chain variable region sequence):
DIQMTQSPSSLSASVGDRVTITCRASQDVRNWLTWYQQKPGKAPKLLIYGASN
LASGVPSRFSGSGSGTDFTLTISSLQPEDFATYYCQQDDSTPPTFGQGTKVEIK SEQ ID NO. 21 (DFSK9-L11 light chain variable region sequence):
DIQMTQSPSSLSASVGDRVTITCRASQSIRSYLNWYQQKPGKAPKLLIYDASSR
PTGVPSRFSGSGSGTDFTLTISSLQPEDFATYYCQQGDSMPMTFGQGTKVEIK
``` ably higher than that of other clones, and five of the single-chain antibodies are selected for next test.

Embodiment 4, In-Vitro Affinity Maturation of Screened Anti-Proprotein Convertase Subtilisin/Kexin Type 9 (PCSK9) Single Chain Antibodies for Another Time 4.1 Establishment of Heavy Chain CDR123 Mutation Libraries by Using a Chain Displacement Method Carrying out double-digestion on mixed plasmid of five single-chain antibodies including DFSK9-2, DFSK9-4, DFSK9-5, DFSK9-6 and DFSK9-8 in the embodiment 3.3 by using NcoI-HF and KpnI, cutting glue, and recycling a strip of 5.5 kb; carrying out double-digestion on a synthetic heavy chain mutation library gene VHCDR123M by using NcoI-HF and KpnI, and recycling a digestion product by using a universal recycling agent kit; connecting the mutation library gene with a vector for 4 hours by using T4 Deoxyribonucleic Acid (DNA) ligase at 16° C. according to a mole ratio of 3:1; transforming connection product into XL1-Blue electrocompetent cells by using an electroporation method; at 37° C., carrying out vibration culture for one hour at 150 rpm to achieve anabiosis; diluting a 1% bacterial liquid, coating a small plate, and calculating a library capacity; centrifuging other bacterial liquid for 15 minutes at 4000 rpm, coating precipitate to a 2YTATG large plate, inverting and culturing at 37° C. overnight; the established antibody library has a library capacity about $5*10^8$, randomly selecting 20 clones to carry out sequence analysis, and both a sequence accuracy rate and diversity are greater than 90%.

4.2 Biopanning of Phage Antibody Libraries and Screening of Positive Clones

Carrying out phage display and purification on the antibody library in the embodiment 4.1; panning anti-PCSK9 single-chain antibodies; a biopanning method of the phage antibody library and screening of the positive clones are identical to those of the embodiment 1 and the embodiment 2; sequencing to screen 10 different anti-PCSK9 antibody sequences which are respectively named as DFSK9-12, DFSK9-13, DFSK9-14, DFSK9-15, DFSK9-16, DFSK9-17, DFSK9-18, DFSK9-19, DFSK9-20 and DFSK9-21; herein, DFSK9-12 has a light chain variable region sequence of DFSK9-L2, and the corresponding amino acid sequence is shown in SEQ ID NO. 12; DFSK9-13 has a light chain variable region sequence of DFSK9-L8, and the corresponding amino acid sequence is shown in SEQ ID NO. 18; DFSK9-14, DFSK9-16 and DFSK9-18 have a light chain variable region sequence of DFSK9-L5, and the corresponding amino acid sequence is shown in SEQ ID NO. 15; DFSK9-15, DFSK9-17, DFSK9-20 and DFSK9-21 have a light chain variable region sequence of DFSK9-L6, and the corresponding amino acid sequence is shown in SEQ ID NO. 16; DFSK9-19 has a light chain variable region sequence of DFSK9-L4, and the corresponding amino acid sequence is shown in SEQ ID NO. 14. DFSK9-12 has a heavy chain variable region sequence of DFSK9-H2, and corresponding amino acid sequence is shown in SEQ ID NO. 2; DFSK9-13 has a heavy chain variable region sequence of DFSK9-H8, and the corresponding amino acid sequence is shown in SEQ ID NO. 8; DFSK9-14 has a heavy chain variable region sequence of DFSK9-H7, and the corresponding amino acid sequence is shown in SEQ ID NO. 7; DFSK9-15 has a heavy chain variable region sequence of DFSK9-H3, and the corresponding amino acid sequence is shown in SEQ ID NO. 3; DFSK9-16 has a heavy chain variable region sequence of DFSK9-H6, and the corresponding amino acid sequence is shown in SEQ ID NO. 6; DFSK9-17 and DFSK9-18 have a heavy chain variable region sequence of DFSK9-H4, and the corresponding amino acid sequence is shown in SEQ ID NO. 4; DFSK9-19 has a heavy chain variable region of DFSK9-H9, and the corresponding amino acid sequence is shown in SEQ ID NO. 9; DFSK9-20 has a heavy chain variable region of DFSK9-H5, and the corresponding amino acid sequence is shown in SEQ ID NO. 5; DFSK9-21 has a heavy chain variable region sequence of DFSK9-H10, and the corresponding amino acid sequence is shown in SEQ ID NO. 10. Light chain variable region sequences are shown in amino acid sequence SEQ ID NO. 12, SEQ ID NO. 14, SEQ ID NO. 15, SEQ ID NO. 16 and SEQ ID NO. 18 in the embodiment 3.2, and heavy chain variable region amino acid sequences SEQ ID NO. 2-SEQ ID NO. 10 are as follows:

```
SEQ ID NO. 2 (DFSK9-H2 heavy chain variable region sequence):
QVQLVQSGAEVKKPGASVKVSCKASGYTVTSYGISWVRQAPGQGLEWMGWL
SFYNGNTNYAQKLQGRGTMTTDPSTSTAYMELRSLRSDDTAVYYCARGYSLDV
WGQGTTVTSS SEQ ID NO. 3 (DFSK9-H3 heavy chain variable region sequence):
QVQLVQSGAEVKKPGASVKVSCKASGYTVTSYGISWVRQAPGQ
GLEWMGWVSFYNGQTNYAQKLQGRGTMTTDPSTSTAYMELRSLRSDDTAVYYCA
RGYSLDVWGQGTTVTSS SEQ ID NO. 4 (DFSK9-H4 heavy chain variable region sequence):
QVQLVQSGAEVKKPGASVKVSCKASGYTVTSYGISWVRQAPGQ
GLEWMGWVSFYNGNSNYAQKLQGRGTMTTDPSTSTAYMELRSLRSDDTAVYYCA
RGYSLDVWGQGTTVTSS SEQ ID NO. 5 (DFSK9-H5 heavy chain variable region sequence):
QVQLVQSGAEVKKPGASVKVSCKASGYSLTSYGISWVRQAPGQ
GLEWMGWVSFYNGNSNYAQKLQGRGTMTTDPSTSTAYMELRSLRSDDTAVYYC
RGFGMDRWGQGTTVTSS SEQ ID NO. 6 (DFSK9-H6 heavy chain variable region sequence):
QVQLVQSGAEVKKPGASVKVSCKASGYTVTSYGISWVRQAPGQGLEWMGWV
SFYQGNTNYAQKLQGRGTMTTDPSTSTAYMELRSLRSDDTAVYYCARGFGMDRW
GQGTTVTSS
```

-continued

```
SEQ ID NO. 7 (DFSK9-H7 heavy chain variable region sequence):
QVQLVQSGAEVKKPGASVKVSCKASGYSLTSYGISWVRQAPGQGLEWMGWV
SFYNGQTNYAQKLQGRGTMTTDPSTSTAYMELRSLRSDDTAVYYCARGYGMSIW
GQGTTVTVSS SEQ ID NO. 8 (DFSK9-H8 heavy chain variable region sequence):
QVQLVQSGAEVKKPGASVKVSCKASGYSLTSYGISWVRQAPGQGLEWMGWV
SFYQGNTNYAQKLQGRGTMTTDPSTSTAYMELRSLRSDDTAVYYCARGYGMTVW
GQGTTVTVSS SEQ ID NO. 9 (DFSK9-H9 heavy chain variable region sequence):
QVQLVQSGAEVKKPGASVKVSCKASGYSLTSYGISWVRQAPGQGLEWMGWV
TFYNGNTNYAQKLQGRGTMTTDPSTSTAYMELRSLRSDDTAVYYCARGFGLSVWG
QGTTVTVSS SEQ ID NO. 10 (DFSK9-H10 heavy chain variable region sequence):
QVQLVQSGAEVKKPGASVKVSCKASGYSLTSYGISWVRQAPGQGLEWMGWV
SFYNGQTNYAQKLQGRGTMTTDPSTSTAYMELRSLRSDDTAVYYCARGFGMDRW
GQGTTVTVSS
```

Figure 4:
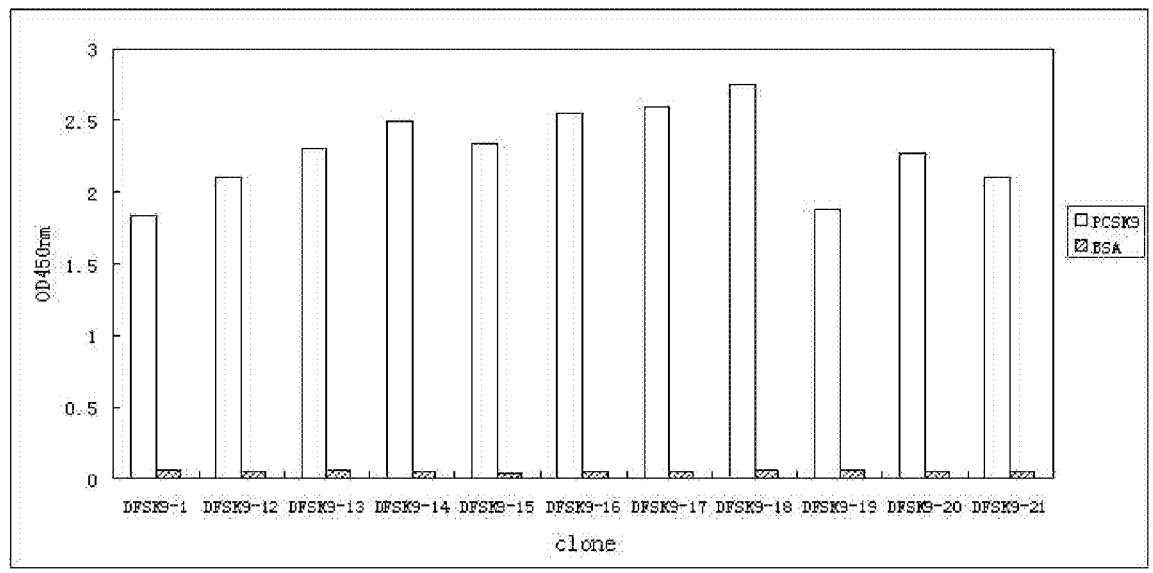
FIG. 4 shows identification of relative affinity of the single-chain antibody of an antibody library of a mutant heavy chain by means of positive cloning phage monoclonal (ELISA)

Monoclonal phage ELISA identification on relative affinity of phage-Abs is shown in FIG. 4.

Figure 5:
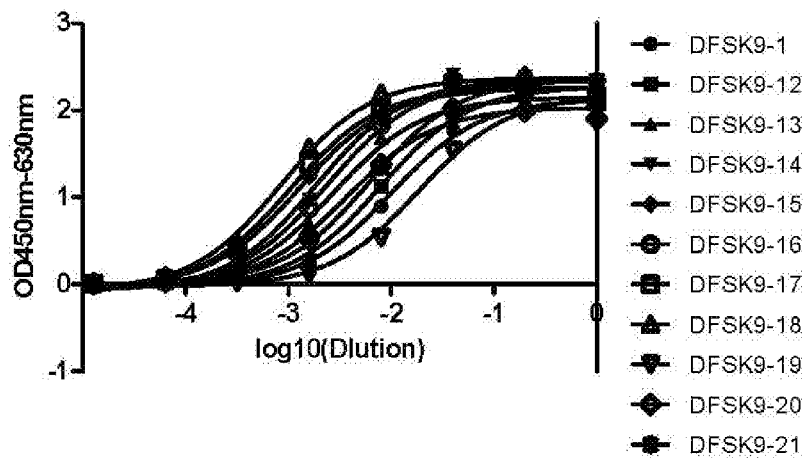
FIG. 5 shows relative affinity comparison of the single-chain antibody of the antibody library of the mutant heavy chain by means of positive cloning phage monoclonal gradient diluted ELISA.

4.3 Gradient Diluted Phage ELISA Identification on Affinity of the PCSK9 Single Chains Antibodies Carrying out monoclonal phage display and purification on the clones obtained in the embodiment 4.2, and carrying out phage horizontal gradient diluted ELISA identification on affinity of the single chain antibody, by using the same methods as those in the embodiment 3.3 of the embodiment 3. Results are shown in FIG. 5. The ten different screened single-chain antibodies all are capable of well binding with the PCSK9 and have higher affinity than that of primary single-chain DFSK9-1.

Embodiment 5, Affinity Identification the of the Completeanti-Proprotein Convertase Subtilisin/Kexin Type 9 (PCSK9) Antibodies

5.1 Preparation of the Complete Antibodies of the Anti-PCSK9

Figure 6:
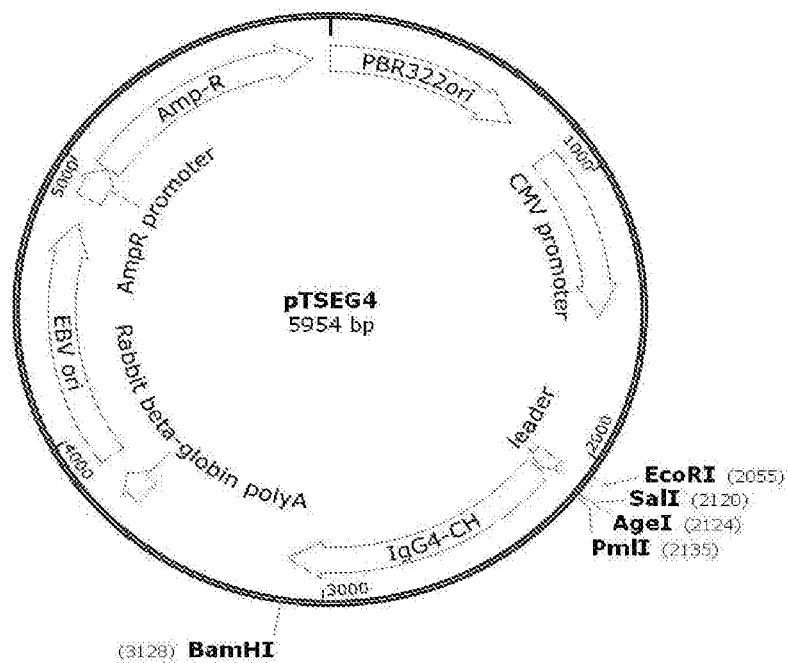
FIG. 6 shows a pTSEG4 plasmid profile.
Figure 7:
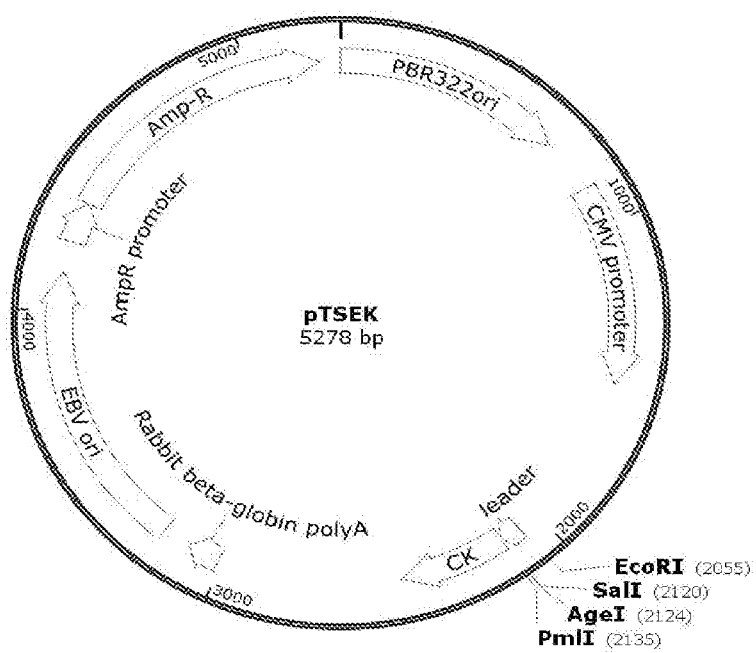
FIG. 7 shows a pTSEK plasmid profile.

Cloning the heavy chain VH gene of the antibody screened in the embodiment 4 into the vector pTSEG4 (FIG. 6) which having a heavy chain constant region gene (γ4), cloning the light chain VK gene into the vector pTSEK (FIG. 7) which having a light chain constant region gene (κ chain), and both the vectors pTSEG4 and pTSEK are obtained by means of transformation on the basis of the PTT vector. The preparation process of the PTT vector is specifically described in a reference (Yves.Durocher, Sylvie.Perret and Amine.Kamen Nucleic Acids Research, 2002 Vol. 30, No. 2e9). Carrying out transient transfection on the HEK293E cell, carrying out complete antibody expression, and purifying by using an AKTA protein a affinity column to obtain complete antibody proteins.

5.2 Binding Test of Complete Antibodies with PCSK9

Figure 8:
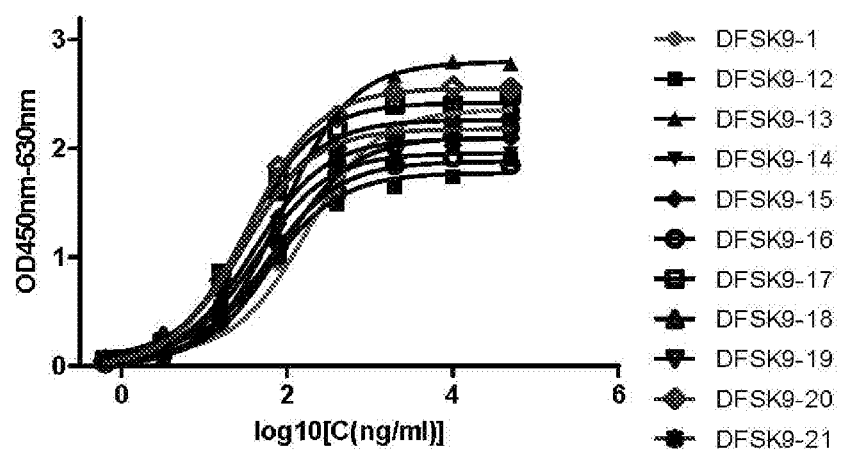
FIG. 8 shows binding test of the complete anti-Proprotein Convertase Subtilisin/Kexin Type 9 (PCSK9) antibody with PCSK9 at the molecular level.

Coating PCSK9-His (300 ng/well/100 µl) by 0.01M PBS buffer at pH 7.2 overnight at 4° C., washing three times with PBST (1‰ Tween 20) of 300 µl/well, further adding PBST-4% milk, and blocking for one hour at 37° C.; adding complete antibodies DFSK9-1, DFSK9-12, DFSK9-13, DFSK9-14, DFSK9-15, DFSK9-16, DFSK9-17, DFSK9-18, DFSK9-19, DFSK9-20 and DFSK9-21 of different dilution degrees; the highest concentration of the 11 complete antibodies is 50 µg/ml, diluting at a five-time gradient, diluting for eight gradients for each complete antibody, and incubating for one hour at 37° C.; washing 5 times with PBST of 300 µl/well, further adding a goat-anti-human IgG-HRP secondary antibody diluted by PBST-4% milk at a ratio of 1:5000, and incubating for one hour at 37° C.; washing 5 times with PBST of 300 µl/well, developing by using a Tetramethylbenzidine (TMB) developing kit (100 µl/well), developing for 10 minutes at a room temperature, and terminating developing with 2M $H_2SO_4$ (50 µl/well); reading numbers by using a microplate reader at wavelengths of 450 nm and 630 nm; analyzing data and drawing pictures by using software GraphPad Prism 5Demo, and results are shown in FIG. 8 and table 2. Results show that all antibodies are capable of well binding with PCSK9, and DFSK9-14, DFSK9-15, DFSK9-16, DFSK9-17, DFSK9-18, DFSK9-20 and DFSK9-21 have high affinity.

TABLE 2

| Affinity $EC_{50}$ value of complete antibodies | | |
|---|---|---|
| No. | Sample | $EC_{50}$(ng/ml) |
| 1 | DFSK9-1 | 170.8 |
| 2 | DFSK9-12 | 64.65 |
| 3 | DFSK9-13 | 83.51 |
| 4 | DFSK9-14 | 42.22 |
| 5 | DFSK9-15 | 39.74 |
| 6 | DFSK9-16 | 56.21 |
| 7 | DFSK9-17 | 31.41 |
| 8 | DFSK9-18 | 33.9 |
| 9 | DFSK9-19 | 83.16 |
| 10 | DFSK9-20 | 33.73 |
| 11 | DFSK9-21 | 28.2 |

5.3 the Test of Complete Antibodies Inhibiting the Binding Between Low Density Lipoprotein Receptor (LDLR) and PCSK9

Figure 9:
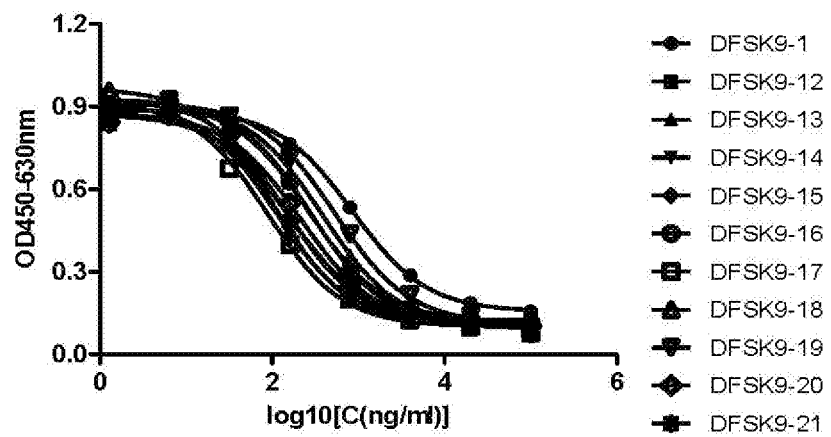
FIG. 9 shows the anti-PCSK9 antibody competitively inhibiting the binding between Low Density Lipoprotein Receptor (LDLR) and the PCSK9.

Coating LDLR-Fc (100 ng/well/100 µl) by 0.01M PBS buffer at pH 7.2 overnight at 4° C., washing three times with PBST, further adding PBST-4% milk, and blocking for one hour at 37° C.; further adding 2 µg/ml PCSK9-His (100 µl well) diluted by PBST-4% milk, and incubating to one hour at 37° C.; adding complete antibodies DFSK9-1, DFSK9-12, DFSK9-13, DFSK9-14, DFSK9-15, DFSK9-16, DFSK9-17, DFSK9-18, DFSK9-19, DFSK9-20 and DFSK9-21 of different dilution degrees; the highest concentration of the 11 complete antibodies is 100 μg/ml, diluting at a five-time gradient, diluting for eight gradients for each complete antibody, and incubating for 2 hours at 37° C.; washing 5 times with PBST, further adding a mouse-anti His IgG-HRP secondary antibody diluted by PBST-4% milk, and incubating for 1 hour at 37° C.; developing by using the TMB developing kit (100 μl/well), developing for 10 minutes at the room temperature, and terminating developing with 2M $H_2SO_4$ (50 μl/well); reading numbers by using the microplate reader at 450 nm and 630 nm; analyzing data and drawing pictures by using software GraphPad Prism 5 Demo, and results are shown in FIG. 9 and table 3. Results show that all antibodies can effectively inhibit binding of the PCSK9 with the LDLR, and DFSK9-14, DFSK9-15, DFSK9-16, DFSK9-17, DFSK9-18, DFSK9-20 and DFSK9-21 have higher inhibition capabilities.

TABLE 3

$IC_{50}$ value of competitive testing of complete antibodies

| No. | Sample | $IC_{50}$(ng/ml) |
|---|---|---|
| 1 | DFSK9-1 | 847.4 |
| 2 | DFSK9-12 | 266.2 |
| 3 | DFSK9-13 | 382.8 |
| 4 | DFSK9-14 | 145.9 |
| 5 | DFSK9-15 | 113.9 |
| 6 | DFSK9-16 | 281.7 |
| 7 | DFSK9-17 | 88.98 |
| 8 | DFSK9-18 | 107.5 |
| 9 | DFSK9-19 | 533.5 |
| 10 | DFSK9-20 | 216.3 |
| 11 | DFSK9-21 | 161.3 |

5.4 Affinity Test of Complete Antibodies by Means of BIAcore X100

Affinity test of complete antibodies by using a capturing method; coupling goat-anti-human IgG to a surface of a CM5 chip, respectively diluting DFSK9-1, DFSK9-12, DFSK9-13, DFSK9-14, DFSK9-15, DFSK9-16, DFSK9-17, DFSK9-18, DFSK9-19, DFSK9-20 and DFSK9-21, and ensuring that about 200RU of the antibodies are captured by the goat-anti-human IgG; setting a series of concentration gradients (200 nM, 100 nM, 50 nM, 25 nM, 12.5 nM, 6.25 nM, 3.125 nM, 1.5625 nM, 0.78125 nM) for PCSK9, flowing through a surface of a stationary phase, and testing the affinity of the antibodies. Results show that the screened antibodies all have high affinity (see table 4), and eight complete antibodies having the highest affinity are selected for bioactivity test.

TABLE 4

Constant test values of affinity of anti-PCSK9 complete antibodies

| No. | Sample | ka (1/Ms) | kd (1/s) | KD (M) |
|---|---|---|---|---|
| 1 | DFSK9-1 | 5.178E+5 | 9.191E-5 | 1.755E-10 |
| 2 | DFSK9-12 | 4.180E+5 | 4.975E-5 | 1.190E-10 |
| 3 | DFSK9-13 | 5.747E+5 | 2.990E-5 | 5.202E-11 |
| 4 | DFSK9-14 | 2.700E+6 | 7.901E-5 | 2.926E-11 |
| 5 | DFSK9-15 | 5.425E+5 | 4.746E-6 | 8.749E-12 |
| 6 | DFSK9-16 | 1.217E+6 | 5.613E-5 | 4.613E-11 |
| 7 | DFSK9-17 | 1.184E+6 | 1.844E-6 | 1.557E-12 |

TABLE 4-continued

Constant test values of affinity of anti-PCSK9 complete antibodies

| No. | Sample | ka (1/Ms) | kd (1/s) | KD (M) |
|---|---|---|---|---|
| 8 | DFSK9-18 | 5.117E+5 | 1.992E-6 | 3.893E-12 |
| 9 | DFSK9-19 | 3.952E+5 | 7.339E-5 | 1.857E-10 |
| 10 | DFSK9-20 | 9.252E+5 | 1.451E-5 | 1.568E-11 |
| 11 | DFSK9-21 | 5.918E+5 | 4.239E-6 | 7.162E-12 |

Figure 10:
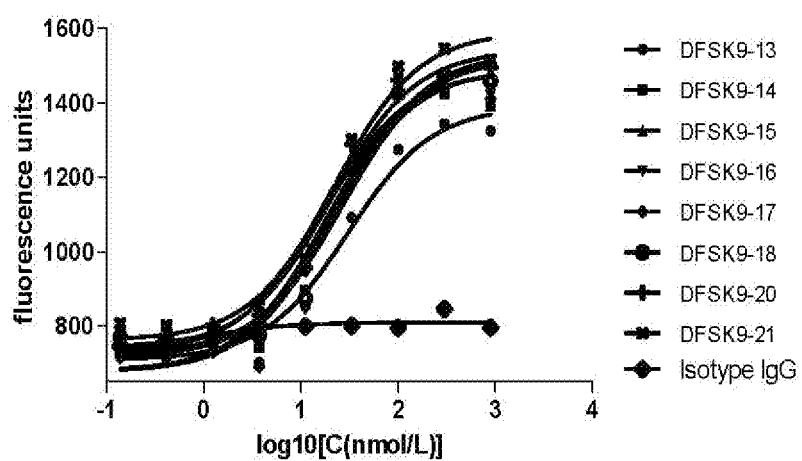
FIG. 10 shows biological activity test of the complete anti-PCSK9 antibody.

Embodiment 6, Bioactivity Test of Complete Anti-Proprotein Convertase Subtilisin/Kexin Type 9 (PCSK9) Antibodies Inoculating HepG2 cell into 96 wells at a ratio of $2.5 \times 10^5$ cells/ml; on a next day, replacing a 10% FBS Mem Ebss Minimum Essential Medium (EMEM) growth culture medium by a 80 μl analysis culture medium of 5% Fetal Bovine Serum (FBS), and culturing for 24 hours at 37° C.; on a next day, putting complete antibodies (10 μl/well) diluted by the analysis culture medium with different dilution degrees into an inoculated HepG2 cell culture plate. Eight complete antibody samples have an initial concentration of 900 nmol/L, diluting at a three-time gradient, and diluting each complete antibody for eight gradients; further adding a 30 nmol/L PCSK9 solution (10 μl/well), uniformly mixing, and culturing for 4 hours at 37° C. in the presence of 5% $CO_2$; adding 10 ul of an Low Density Lipoprotein (LDL) solution marked by 0.1 mg/m L Boron Dipyrromethene (BODIPY), uniformly mixing, and continuously culturing for 15-20 hours in the presence of 5% $CO_2$ at 37° C.; adding 200 μl of the PBS into each well, washing twice, adding 100 μl of the PBS into each well, reading Relative Fluorescent Unit (RFU) values by using a microplate reader at wavelengths of 490 nm and 520 nm; analyzing data and drawing diagrams by using software GraphPad Prism 5Demo, and demonstrating results in FIG. 10. As negative control with homologous IgG, the diagrams show that the eight antibodies all can block binding of the PCSK9 with the LDLR in a dose-dependent manner and increase an intake rate of the LDL in the HepG2 cell, and the antibodies have approximate bioactivity.

TABLE 5

$EC_{50}$ value of bioactivity testing

| No. | Sample | $EC_{50}$(nmol/L) |
|---|---|---|
| 1 | DFSK9-13 | 29.61 |
| 2 | DFSK9-14 | 16.59 |
| 3 | DFSK9-15 | 15.31 |
| 4 | DFSK9-16 | 23.80 |
| 7 | DFSK9-17 | 18.51 |
| 8 | DFSK9-18 | 23.91 |
| 9 | DFSK9-20 | 17.95 |
| 10 | DFSK9-21 | 20.33 |

For ordinary persons skilled in the art, the embodiments only exemplarily describe the disclosure, and obviously the specific implementation of the present disclosure is not limited by the above-mentioned methods. Any non-substantive improvement on the basis of method conception and technical schemes of the disclosure, or disclosures of the method conception and the technical schemes of the disclosure without improvement to other situations shall fall within the scope of protection of the disclosure.

What is claimed is:

1. An anti-PCSK9 monoclonal antibody, comprising: a light chain and a heavy chain, the light chain has Light Complementarity-Determining Regions CDR1, CDR2 and CDR3 represented by LCDR1, LCDR2 and LCDR3 respectively; in addition, the heavy chain has CDR1, CDR2 and CDR3 represented by HCDR1, HCDR2 and HCDR3 respectively; LCDR1, LCDR2, LCDR3, HCDR1, HCDR2 and HCDR3 of the anti-PCSK9 monoclonal antibody are selected from the following group:

a first group is PCSK9-15, comprising: HCDR1: SEQ ID NO:54; HCDR2: SEQ ID NO:60; HCDR3: SEQ ID NO:63; LCDR1: SEQ ID NO:27; LCDR2: SEQ ID NO:37; LCDR3: SEQ ID NO:47;

a second group is PCSK9-17, comprising: HCDR1: SEQ ID NO:54; HCDR2: SEQ ID NO:61; HCDR3: SEQ ID NO:63; LCDR1: SEQ ID NO:27; LCDR2: SEQ ID NO:37; LCDR3: SEQ ID NO:47;

a third group is PCSK9-20, comprising: HCDR1: SEQ ID NO:55; HCDR2: SEQ ID NO:61; HCDR3: SEQ ID NO:65; LCDR1: SEQ ID NO:27; LCDR2: SEQ ID NO:37; LCDR3: SEQ ID NO:47; and a fourth group is PCSK9-21, comprising: HCDR1: SEQ ID NO:55; HCDR2: SEQ ID NO:60; HCDR3: SEQ ID NO:65; LCDR1: SEQ ID NO:27; LCDR2: SEQ ID NO:37; LCDR3: SEQ ID NO:47.

2. The anti-PCSK9 monoclonal antibody as claimed in claim 1, wherein the light chain variable region amino acid sequence is selected from any one of SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 or SEQ ID NO:21.

3. The anti-PCSK9 monoclonal antibody as claimed in claim 1, wherein the heavy chain variable region amino acid sequence is selected from any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 or SEQ ID NO:10.

4. An antibody, a polypeptide, a protein, an antibody drug conjugate, an artificial carrier, a medicine or a medicine composition comprising the anti-PCSK9 monoclonal antibody as claimed in claim 1.

5. The anti-PCSK9 monoclonal antibody as claimed in claim 1, wherein the anti-PCSK9 monoclonal antibody is whole-length antibody, single-chain antibody, single domain antibody, or bispecific antibody.

6. The anti-PCSK9 monoclonal antibody as claimed in claim 1, wherein a polynucleotide sequence for encoding the anti-PCSK9 monoclonal antibody as claimed in claim 1 is inserted in a recombinant DNA expression vector.

7. The anti-PCSK9 monoclonal antibody as claimed in claim 6, wherein the recombinant DNA expression vector is transfected in a host cell, wherein the host cell comprises a prokaryotic cell, a yeast, an insect cell or a mammalian cell.

8. The anti-PCSK9 monoclonal antibody as claimed in claim 7, wherein the prokaryotic cell is an *Escherichia coli*; the mammalian cell is a HEK293 cell, a CHO cell or a NS0 cell.

9. The anti-PCSK9 monoclonal antibody as claimed in claim 1, wherein the heavy chain constant region of the anti-PCSK9 monoclonal antibody comprises IgG1, IgG2, IgG3 or IgG4; the light chain constant region comprises $C_K$ or $C_\lambda$.

10. The anti-PCSK9 monoclonal antibody as claimed in claim 9, wherein the heavy chain constant region comprises IgG4 or IgG2; the light chain constant region comprises $C_K$.

11. The anti-PCSK9 monoclonal antibody as claimed in claim 1, wherein the monoclonal antibody comprises a whole-length antibody or a fragment of the anti-PCSK9 monoclonal antibody, and the fragment comprises one or a combination of Fab, Fab', $F(ab)_2$, Fv and ScFv.

12. A detection reagent or a kit comprising the anti-PCSK9 monoclonal antibody as claimed in claim 1.

13. An antibody comprising the anti-PCSK9 monoclonal antibody as claimed in claim 1, for eliminating, inhibiting or reducing activity of the PCSK9 and alleviating, relieving, inhibiting or preventing diseases; the diseases comprise dyslipidemia, cardiovascular and cerebrovascular diseases and thrombotic occlusive diseases.

\* \* \* \* \*